United States Patent
Latella, Jr.

(10) Patent No.: US 11,266,328 B2
(45) Date of Patent: Mar. 8, 2022

(54) SYSTEMS AND METHODS FOR EVALUATING BODY MOTION

(71) Applicant: Latella Sports Technologies, LLC, Wilton, CT (US)

(72) Inventor: Frank A. Latella, Jr., Wilton, CT (US)

(73) Assignee: Latella Sports Technologies, LLC, Wilton, CT (US)

( * ) Notice: Subject to any disclaimer, the term of this patent is extended or adjusted under 35 U.S.C. 154(b) by 126 days.

(21) Appl. No.: 16/054,074

(22) Filed: Aug. 3, 2018

(65) Prior Publication Data
US 2019/0038187 A1   Feb. 7, 2019

Related U.S. Application Data

(60) Provisional application No. 62/540,689, filed on Aug. 3, 2017.

(51) Int. Cl.
*G06K 9/00* (2006.01)
*A61B 5/11* (2006.01)
(Continued)

(52) U.S. Cl.
CPC .......... *A61B 5/1128* (2013.01); *A61B 5/1121* (2013.01); *A61B 5/7425* (2013.01);
(Continued)

(58) Field of Classification Search
CPC ... A61B 5/0077; A61B 5/1114; A61B 5/1121; A61B 5/1128; A61B 5/7425; A61B 2505/09; A61B 2576/00; A63B 2024/0068; A63B 2071/065; A63B 2220/806; A63B 24/0062; G06F 3/011; G06F 3/0346;
(Continued)

(56) References Cited

U.S. PATENT DOCUMENTS

| 9,773,330 | B1* | 9/2017 | Douglas | G06F 3/0346 |
| 2006/0161363 | A1* | 7/2006 | Shibasaki | G01C 19/5607 |
| | | | | 702/94 |

(Continued)

OTHER PUBLICATIONS

Lynley, Matthew, Enflux, a Smart Body-tracking Workout Outfit, Launches on Kickstarter:, accessed Aug. 2, 2018, https://techcrunch.com/2016/03/07/enflux-a-smart-body-tracking-workout-outfit-launches-on-kickstarter/.
(Continued)

*Primary Examiner* — Tom Y Lu
(74) *Attorney, Agent, or Firm* — DLA Piper LLP (US)

(57) ABSTRACT

The present disclosure is directed towards computer-based systems and methods for evaluating a user's body motion based on motion data obtained via a series of wireless sensors attached to a user's body. In one embodiment, a computer-implemented method is disclosed herein. A server system receives motion data from one or more input devices. The motion data corresponds to movement of a user. The server system generates a motion profile based on at least the motion data received from the one or more input devices. The server system retrieves a pre-defined target motion profile from a database structure. The server system objectively evaluating the extracted motion profile by comparing one or more parameters of the generated motion profile with one or more parameters of the retrieved pre-defined target motion profile.

16 Claims, 21 Drawing Sheets

(51) Int. Cl.
  *G06T 7/246* (2017.01)
  *G06T 7/73* (2017.01)
  *A63B 24/00* (2006.01)
  *A61B 5/00* (2006.01)
  *G06F 3/01* (2006.01)
  *G06F 3/0346* (2013.01)
  *A63B 71/06* (2006.01)

(52) U.S. Cl.
  CPC .......... *A63B 24/0062* (2013.01); *G06F 3/011* (2013.01); *G06F 3/0346* (2013.01); *G06T 7/248* (2017.01); *G06T 7/74* (2017.01); *A61B 5/0077* (2013.01); *A61B 5/1114* (2013.01); *A61B 2505/09* (2013.01); *A61B 2576/00* (2013.01); *A63B 2024/0068* (2013.01); *A63B 2071/065* (2013.01); *A63B 2220/806* (2013.01); *G06T 2207/20072* (2013.01); *G06T 2207/30196* (2013.01)

(58) Field of Classification Search
  CPC ............ G06F 3/03545; G06F 3/03547; G06F 3/0383; G06F 3/0412; G06F 3/0414; G06F 3/0416; G06F 3/04182; G06F 3/04184; G06F 3/044; G06F 3/0446; G06T 2207/20072; G06T 2207/30196; G06T 7/248; G06T 7/74; G09G 2310/0264
  See application file for complete search history.

(56) References Cited

U.S. PATENT DOCUMENTS

| | | | | |
|---|---|---|---|---|
| 2010/0277411 | A1* | 11/2010 | Yee | G06K 9/00912 345/156 |
| 2013/0217352 | A1* | 8/2013 | Pan | A61B 5/1112 455/404.1 |
| 2014/0228712 | A1* | 8/2014 | Elliott | A63B 71/06 600/587 |
| 2014/0228985 | A1* | 8/2014 | Elliott | A63B 71/06 700/91 |

OTHER PUBLICATIONS

Enflux Motion Capture Clothing, accessed Aug. 2, 2018, https://www.getenflux.com/.

\* cited by examiner

LNTS Prescription
John Doe
Thursday, June 15, 2017, 4:14:20 PM
John's Shoulder Exercises
Sample diagnosis with notes e.g. shoulder had poor flexibility
Exercises
5 x Exercise Title #001
Exercise Description
5 x Exercise Title #002
Exercise Description
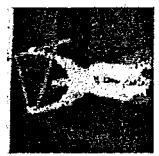
5 x Exercise Title #003
Exercise Description
FIG. 19

SYSTEMS AND METHODS FOR EVALUATING BODY MOTION

CROSS-REFERENCE TO RELATED APPLICATIONS

This application claims reference to U.S. Provisional Application Ser. No. 62/540,689 filed Aug. 3, 2017, which is hereby incorporated by reference in its entirety.

TECHNICAL FIELD

The present disclosure is directed towards computer-based systems and methods for evaluating a user's body motion based on motion data obtained via a series of wireless sensors attached to a user's body. The motion data may objectively evaluated by the computer-based system.

BACKGROUND

Conventionally, a physical therapist or trainer may measure the range of motion and other motion data for a particular joint before, during, and/or after an activity. For example, range of motion may be measured manually using a goniometer. However goniometers measurements may be inaccurate due to poor placement of the goniometer, interference due to uncontrolled movements by the user, and inability to properly obtain measurements using the goniometers. Moreover, goniometer measurements may be subject to both inter-user and intra-user variability. Put simply, a physical therapist or trainer may not measure the range of motion using the same method every time they see the patient, and one physical therapist or trainer may have a different measurement technique than a second physical therapist or trainer. As range of motion and other movement features are important factors for benchmarking progress in patients and athletes it is critical to have the most accurate and objective measurement of range of motion and other movement features.

Indeed, as discussed by Nussbaumer et al. (Nussbaumer, Silvio, et al. "Validity and test-retest reliability of manual goniometers for measuring passive hip range of motion in femoroacetabular impingement patients." BMC musculoskeletal disorders 11.1 (2010): 194.), major drawbacks of goniometry for hip measurements are that the starting position, the center of rotation, the long axis of the limb and the true vertical and horizontal positions can only be visually estimated and that conventional goniometers must be held with two hands, leaving neither hand free for stabilization of the body or the proximal part of the joint. There are also difficulties in monitoring joints that are surrounded by large amounts of soft tissue, such as the hip. The validity (i.e., the degree to which a measurement actually measures what it claims to measure) and reliability (i.e., the degree to which a measurement is consistent and stable) of manual goniometers have therefore been questioned, especially for measuring hip flexion.

Accordingly there remains a need for systems and methods to evaluate a user's body motion in an automated and objective manner such that they are not prone to human error or variation due to human recording.

SUMMARY

In one embodiment, a computer-implemented method is disclosed herein. A server system receives motion data from one or more input devices. The motion data corresponds to movement of a user. The server system generates a motion profile based on at least the motion data received from the one or more input devices. The server system retrieves a pre-defined target motion profile from a database structure. The server system objectively evaluating the extracted motion profile by comparing one or more parameters of the generated motion profile with one or more parameters of the retrieved pre-defined target motion profile.

In another embodiment, a computer-implemented method is disclosed herein. A server system receives motion data from a plurality of input devices positioned about a user while performing a movement. The server system generates a motion profile for the user based at least on the motion data, by calculating a position of a joint of the user's body based on the motion data, calculating positions of at least two reference points of the user's body based on the motion data, and calculating an actual range of motion for the joint based on the position of the joint and the positions of the at least two reference points. The server system retrieves a reference range of motion from a database storing one or more reference range of motions for one or more movements. The system evaluates a user's body motion by comparing the reference range of motion to the actual range of motion to objectively evaluate the user's movement.

In another embodiment, a system is disclosed herein. The system includes one or more input devices, a processor, and a memory. The one or more input devices are configured to capture a movement of a user. The processor in communication with the one or more input devices. The memory has programming instructions stored thereon, which, when executed by the processor, performs an operation. The operation includes receiving motion data from the one or more input devices, the motion data corresponding to movement of a user. The operation further includes generating a motion profile based on at least the motion data received from the one or more input devices. The operation further includes retrieving a pre-defined target motion profile from a database structure. The operation further includes objectively evaluating the extracted motion profile by comparing one or more parameters of the generated motion profile with one or more parameters of the retrieved pre-defined target motion profile.

The present disclosure relates to computer based systems and methods for evaluating a user's body motion in an automated and objective fashion. To that end, a computer-implemented method for automated movement evaluations may extract a motion profile from motion data received from one or more wireless sensors configured to obtain motion information of a user, retrieve a pre-defined target motion profile from a database structure, and objectively evaluate the extracted motion profile by comparing one or more parameters of the extracted motion profile with one or more corresponding parameters of the retrieved pre-defined target motion profile. In one embodiment, the computer-implemented method may be configured to take one or more actions as a result of the objective evaluation.

In one embodiment, the systems and methods described herein may be integrated with the administrative computer systems used by physical therapists, medical professionals, insurance companies and the like. Accordingly, the systems and methods described herein may provide automated coding and billing services to third party providers, and monitor and convey information related to patient compliance and progression.

In one embodiment, the systems and methods described herein may provide means for improving a patient or athlete's performance of a particular movement.

In one embodiment, the computer based system for automated movement evaluations may be integrated with administrative medical computer systems and provide automated billing, insurance, and prescription assistance.

BRIEF DESCRIPTION OF THE DRAWINGS

Many aspects of the present embodiments may be better understood with reference to the following drawings. The components in the drawings are not necessarily to scale, emphasis instead being placed upon illustrating example embodiments:

FIGS. 7-21 show illustrative user interfaces (UIs) that may be used within a body motion evaluation system, according to embodiments of the present disclosure.

DETAILED DESCRIPTION

The present disclosure relates to computer based systems and methods for automated movement evaluations. To that end a computer-implemented method for automated movement evaluations may extract a motion profile from motion data received from one or more wireless sensors configured to obtain motion information of a user, retrieve a pre-defined target motion profile from a database structure, and objectively evaluate the extracted motion profile by comparing one or more parameters of the extracted motion profile with one or more corresponding parameters of the retrieved pre-defined target motion profile. In one embodiment, the computer-implemented method may be configured to take one or more actions as a result of the objected evaluation.

Figure 1:
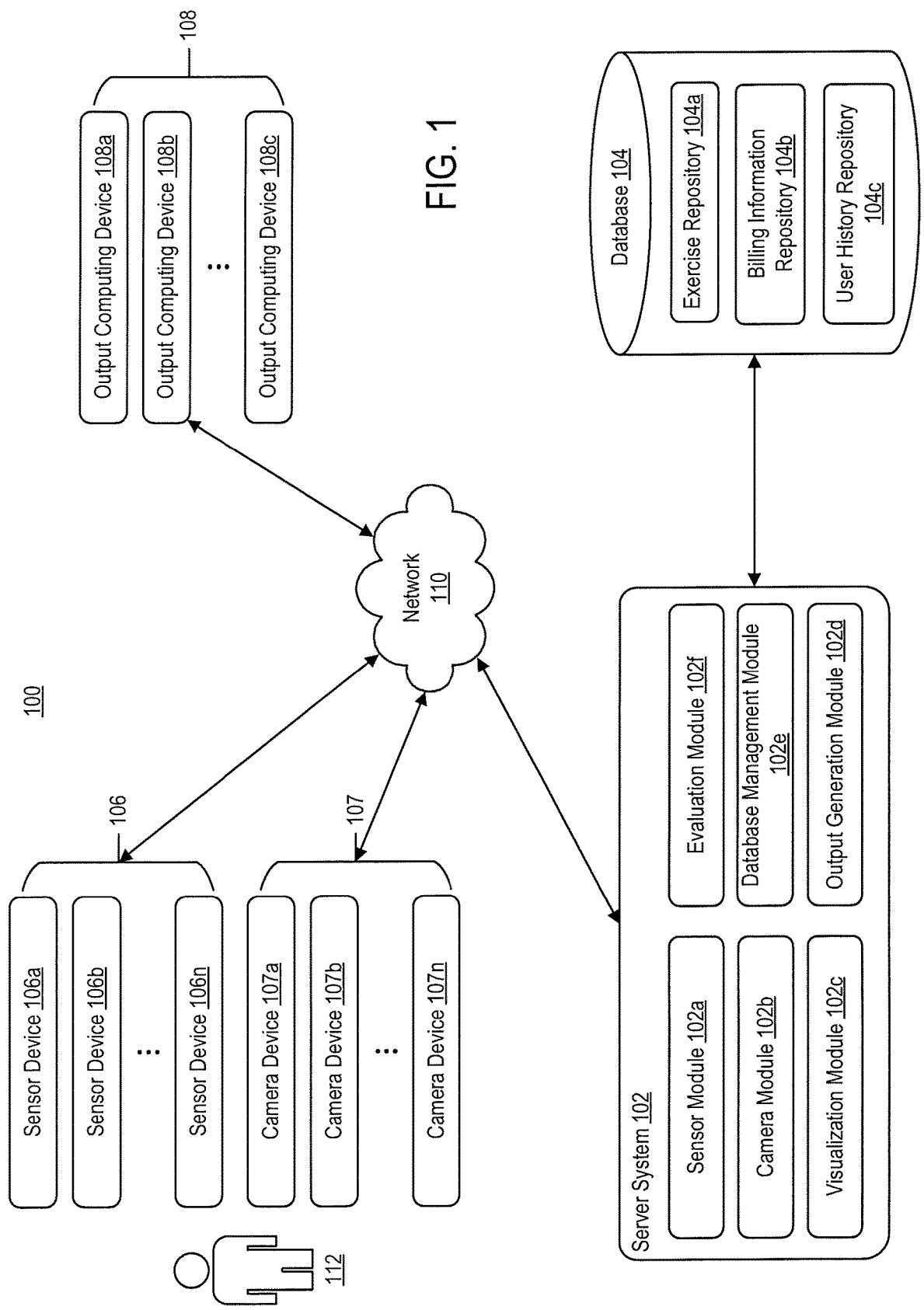
FIG. 1 is a system diagram showing a body motion evaluation system, according to an embodiment of the present disclosure.

FIG. 1 is a system diagram illustrating a body motion evaluation system 100, according to an exemplary embodiment. Body motion evaluation system 100 may include a processing system (or "server") 102, a database 104, a plurality of sensors 106a-106n (106 generally), and a plurality of output devices 108a-108n (108 generally). In some embodiments, the system 100 may also include a plurality of cameras 107a-107n (107 generally). The sensors, cameras, and output devices may be in communication with the server 102 via a network 110.

Network 110 may be of any suitable type, including individual connections via the Internet, such as cellular or Wi-Fi networks. In some embodiments, network 105 may connect terminals, services, and mobile devices using direct connections, such as radio frequency identification (RFID), near-field communication (NFC), Bluetooth™, low-energy Bluetooth™ (BLE), Wi-Fi™, ZigBee™, ambient backscatter communication (ABC) protocols, USB, WAN, or LAN. Because the information transmitted may be personal or confidential, security concerns may dictate one or more of these types of connection be encrypted or otherwise secured. In some embodiments, however, the information being transmitted may be less personal, and therefore, the network connections may be selected for convenience over security.

Network 110 may include any type of computer networking arrangement used to exchange data. For example, network 110 may include any type of computer networking arrangement used to exchange information. For example, network 110 may be the Internet, a private data network, virtual private network using a public network and/or other suitable connection(s) that enables components in body motion evaluation system 100 to send and receiving information between the components of body motion evaluation system 100.

The sensors 106 may be attached to the body of a user 112. In some embodiments, the sensors may be coupled to one or more articles of clothing that can be worn by the user 112. For example, the sensors 106 may be attached to a tight-fighting body suit that can be worn by the user 112. In another example, the sensors 106 may be attached to a sleeve (e.g., arm compression sleeve, calve compression sleeve, quadriceps/hamstring compression sleeve, etc.). In one embodiment, sensors 106 may be located proximate a user's wrist, shoulder and/or back.

Data generated by the sensors 106 and cameras 107 may be provided to the server 102 via the network 110. The illustrative server 102 includes a sensor module 102a, camera module 102b, visualization module 102c, output generation module 102d, database management module 102e, and an evaluation module 102f. The operations described herein may be achieved with any suitable number of modules.

Each of the sensors 106 is configured to generate motion data responsive to the user's body motion. In one embodiment, each of the one or more sensors 106 may include an accelerometer, magnetometer, and/or gyroscope. An accelerometer may be configured to measure acceleration forces at the location of each sensor 106. In some embodiments, the acceleration forces may be measured in units of meters per second-squared ($m/s^2$). In some embodiments, the magnetometer may be configured to measure magnetism and be normalized for Earth's magnetic field. In some embodiments, a gyroscope may be configured to measure angular velocity in units of radians per second ($\omega$). In some embodiments embodiments, a sensor's accelerometer, magnetometer, and/or gyroscope may be provided as MEMS (microelectromechanical systems) inertial sensors. In some embodiments, each sensor 106 may generate roll, pitch and yaw data responsive to the user's body motion at the point on the user's body where the sensor is located.

Each sensor 106 may generate motion data responsive to the user on any suitable time-scale. For example, in one embodiment the sensors 106 may generate motion data on a time-scale of 1,000 data points per second. Sensor motion data may be processed by one or more filtering and/or down-sampling techniques. In some embodiments, Kalman filters may be used. In some embodiments, motion data may be down-sampled to a time-scale of 125 data points per second. In some embodiments, the filtering and/or down sampling techniques may be performed at the site of the sensor 106, prior to each sensor 106 wirelessly transmitting motion data to the server system 102. In some embodiments, the entirety of the obtained sensor motion data may be transmitted to the server system 102 and then filtered and/or down sampled at the server system 102 by a sensor module 102a.

In some embodiments, the sensors 106 may transmit motion data to the server system 102 wirelessly via network 110. For example, sensors 106 may transmit motion data to the server system 102 using Bluetooth®, Wi-Fi, near-field communication (NFC), ZigBee®, or any other suitable wireless communication means.

Although the embodiment illustrated in FIG. 1 includes a single server system 102, those skilled in the art may readily understand that multiple server systems may be used. In some embodiments, the multiple server systems may cooperate to evaluate a user's body motion. For example, a sensor module within a first server system may perform an initial processing of sensor motion data, and a second server system may receive and use the initially processed motion data to perform an evaluation of the user's body motion.

In one embodiment, motion data obtained from the sensors 106 may be converted to "positional data" describing to the position of one or more joints, limbs, and/or other reference points on the user's body. Converting sensor motion data to positional data can be based on knowledge of where the sensors 106 are attached to the user's body, dimensions of the user's body, and/or dimensions of clothing worn by the user onto which the sensors are attached. The position data may, in turn, be used to calculate information (or "joint data") about one or more joints of interest, such as range of motion, velocity, acceleration, or other aspects of angular movements about a joint. Example joints of the interest may include the elbow, wrist, shoulder, hip, knee, and ankle.

In one embodiment, the conversion from sensor motion data to positional data for the joints may involve one or more coordinate transformations. For example, in one embodiment, sensor motion data represented as (roll, pitch yaw) values may be converted to 3D Cartesian positional data, e.g., (x, y, z) values using forward kinematics. In one embodiment, motion data received from the sensors 106 may be converted from (roll, pitch, yaw) values into a Quaternion representation. In one embodiment, motion data represented as Quaternions may then be converted to positional data and/or joint data.

In one embodiment, the joint data may include a measure of the angle formed at a joint by two limbs that connect at the joint. In one embodiment the angle formed at the joint may be calculated based on a triangulation of the angle formed by the position of at least two sensors 106 with respect to the floor or another reference point. In one embodiment the angle formed at the joint may be calculated based on a triangulation of the angle formed by the position of the at least two limbs with respect to the floor or another reference point. Joint data may be obtained from positional data by analyzing the orientation of one or more sensors with respect to the user's limbs and joints. In one embodiment this may require knowledge of a user's limb length. This may include limb calculations based on a user's height and weight. In one embodiment joint data may be calculated based on information statistical population information and anatomy research.

In one embodiment, the described system may calculate an angle for the joint of interest based on the angle formed by two 3D Cartesian vectors e.g., (x, y, z) at the joint of interest. In one embodiment the system may display a triangle in a user interface illustrative of the two 3D Cartesian vectors and the angle for the joint. The angle for the joint may be calculated using mathematical techniques applying dot products, inverse trigonometric functions and radians to degree conversion.

In one embodiment, the described system may calculate a "between" value representative of the angle between a target joint and the next adjacent joint to the target joint. The between value may be calculated based on the angle between two directional vectors. The first directional vector may be calculated by subtracting the position of the previous adjacent joint from the position of the target joint. The second directional vector may be calculated from subtracting the position of the target joint from the position of the target joint.

In one embodiment, the described system may calculate an "extend" value representative of the angle between the direction of the target joint to the next adjacent joint to the target joint. The extend value may also be calculated as an angle between two directional vectors. The first directional vector may be calculated by subtracting the position of the target joint from the position of the previous adjacent joint. The second directional vector may be calculated from subtracting the position of the target joint from the position of the target joint.

In one embodiment, the described system may calculate an "axis" value representative of the measure of the angle formed by the target joint when compared to a given axis. In one embodiment the "axis" value may include a feature that allows a three-dimensional vector to offset the calculation and provide a customized measure of the angle. The axis value may be calculated using 2D (i.e., XY, YZ, XZ) planes used to create a directional vector to measure against the angle in 3D space. In one embodiment the axis value may allow a user to ignore unwanted values in the angle measurement. For example, the axis value may allow a user to ignore any horizontal movements when raising their arm vertically.

The visualization module 102c can generate visualizations of a user body movement based on, for example, calculated joint data. Such visualizations may include 3D avatars, wireframes, and animated avatars/wireframes. In some embodiments, visualization module 102c can generate an animated wireframe of the user's movement having a plurality of nodes determined using positional and/or joint data. The positional and/or joint data may be used to determine the movement of nodes within the animation so that the visualization may accurately illustrate real-time user movement (i.e., movement sensed in real-time) or pre-recorded user movement. In one embodiment, the visualization module 102c may generate a visualization based on input from one or more cameras 107 in addition to positional and/or joint data. Data recorded by the cameras 107 may be transmitted via the network 110 to the server system 102 and processed by camera module 102b before being integrated with positional and/or joint data by the visualization module 102c. A visualization generated by the visualization module 102c may be generated by an output generation module 102d and displayed on one or more output devices 108.

In some embodiments, the visualization module 102c may be configured to generate and overlay multiple different visualizations onto each other. For example, as discussed below, reference motion profiles may be stored in a database 104. The visualization module 102c can overlay (i.e., superimpose) an animation (or other visualization) of stored reference movements with an animation of real-time user movements to facilitate evaluation of the user's range of motion.

In one embodiment, an evaluation module 102f of the server system 102 may be configured to provide an evaluation of a movement recorded by the sensors 106 as will be discussed in relation to FIG. 4.

The database management module 102e of the server system 102 may be configured to interface with a database 104 coupled to the server system 102. The database management module 102e may be used to access, retrieve, and modify data stored in the database 104. The database 104 may include one or more repositories that hold data and information.

An exercise repository 104a of the database 104 may store information about "ideal" (or "perfect" or "target") movements associated with certain exercises that can be performed by a user. Such information is referred to herein as a "motion profile." A motion profile may be embodied as positional data, joint data, visualizations, video, and/or any combination thereof. Motion profiles can be retrieved from the exercise repository 104a and used to generate a visualization of the corresponding "ideal" movements that can be compared in real-time against a user's sensed motion.

In one embodiment the exercise repository 104a of the database 104 may store animation files along with metadata for an exercise. The stored "motion profile" may include information related to the motion including a title, file path, target joint, measurement type, benchmark angles, duration and billing code. In one embodiment the stored animation may include animation for some or all character profiles including a 3D avatar, wireframe, and overlay. In one embodiment the stored animation is in an Enflux recording animation file format (.enfl).

The database 104 may also include a billing information repository 104b that is configured to include billing and insurance information related to particular exercises or groups of exercises. For example, each exercise in the exercise repository 104a may be associated with a Current Procedural Terminology (CPT) code that is compatible with standardized billing practices in the medical fields.

The database 104 may also include a user history repository 104c that is configured to store various information associated with particular users. For example, a user's body motion can be captured and stored as a motion profile with the repository 104c. Similar to the "ideal" motion profiles discussed above, the user's historical motion profiles can be compared against subsequent real-time motion for evaluation purposes. Other user information that could be stored includes the user's account registration information, prescribed exercises and training/physical therapy protocols, and billing and insurance information.

In some embodiments, an output generation module 102d may process the information obtained by the server 102 and create the appropriate output for one or more output computing devices 108. For example, an output computing device 108 may include a patient/athlete computer device, an insurance company computing device, and the like. In one embodiment, the output generation module 102d may produce an application, website, or the like for a user, medical professional, or insurance agency personnel to view data and information related to movement. The output generation module 102d may generate prescriptions, directly bill insurance companies, and display exercises on an output computing device 108. Example outputs generated by the output generation module 102d are illustrated in FIGS. 7-22.

In some embodiments, the server system 102 may include one or more processors, or microprocessors coupled to one or more non-transitory memory devices, and may be adapted to perform the functions described herein. A server system 102 may be any special-purpose machine capable of storing and executing a set of computer-readable instructions (e.g., software) that specify actions to be taken to perform the functions described herein. Alternatively, the server system 102 may be a specialized component specifically designed to optimize the relationships set forth herein. The term "server" shall also be taken to include any collection of machines that individually or jointly execute a set (or multiple sets) of instructions to perform any one or more of the methodologies discussed herein. In some examples, at least two of the multiple server systems may be in different physical locations.

A server system 102 is one example of computer-readable storage medium. The term "computer-readable storage medium" should be taken to include a single medium or multiple media that store one or more sets of instructions. The term "computer-readable storage medium" shall also be taken to include any medium that is capable of storing or encoding a set of instructions for execution by the machine and that causes the machine to perform any one or more the methodologies of the present disclosure.

Figure 2:
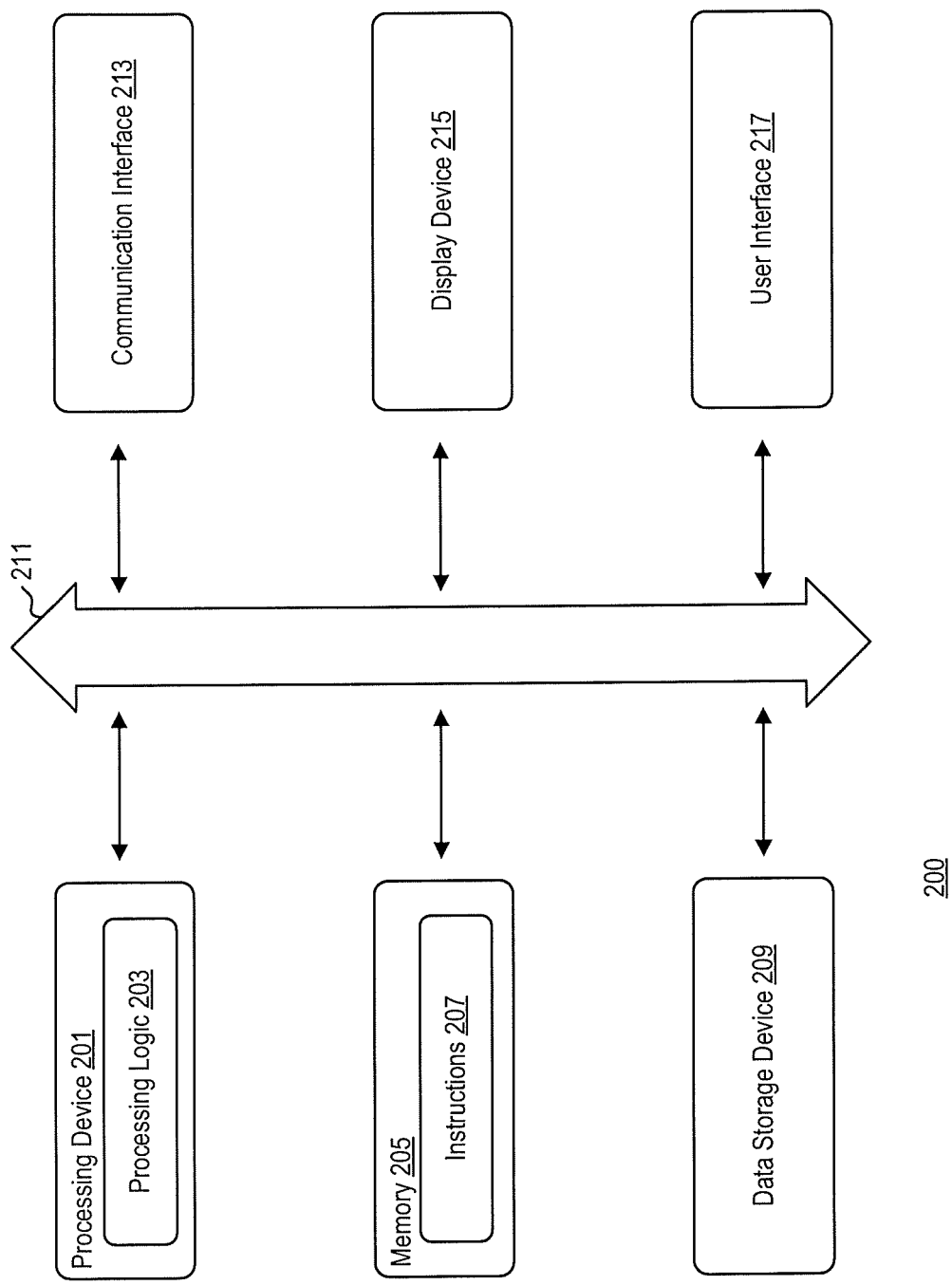
FIG. 2 is a system diagram of an illustrative computer system, according to another embodiment of the present disclosure.

FIG. 2 show an example of a computer system 200, according to an aspect of the present disclosure. In some embodiments, computer system 200 may be the same as or similar to a computer system utilized by a sensor device 106, camera device 107, output device 108, and/or server system 102 of FIG. 1.

The computer system 200 is an example of a machine within which a set of instructions for causing the machine to perform any one or more of the methodologies, processes or functions discussed herein may be executed. In some examples, the machine may be connected (e.g., networked) to other machines as described above. The machine may operate in the capacity of a server or a client machine in a client-server network environment, or as a peer machine in a peer-to-peer (or distributed) network environment. The machine may be any special-purpose machine capable of executing a set of instructions (sequential or otherwise) that specify actions to be taken by that machine for performing the functions describe herein. Further, while only a single machine is illustrated, the term "machine" shall also be taken to include any collection of machines that individually or jointly execute a set (or multiple sets) of instructions to perform any one or more of the methodologies discussed herein. In some examples, each of the output computing devices 108 may be implemented by the example machine shown in FIG. 2 (or a combination of two or more of such machines).

Example computer system 200 may include processing device 201, memory 205, data storage device 209 and communication interface 213, which may communicate with each other via data and control bus 211. In some examples, computer system 200 may also include display device 215 and/or user interface 217.

Processing device 201 may include, without being limited to, a microprocessor, a central processing unit, an application specific integrated circuit (ASIC), a field programmable gate array (FPGA), a digital signal processor (DSP) and/or a network processor. Processing device 201 may be configured to execute processing logic 203 for performing the operations described herein. In general, processing device 201 may include any suitable special-purpose processing device specially programmed with processing logic 203 to perform the operations described herein.

Memory 205 may include, for example, without being limited to, at least one of a read-only memory (ROM), a random access memory (RAM), a flash memory, a dynamic RAM (DRAM) and a static RAM (SRAM), storing computer-readable instructions 207 executable by processing device 201. In general, memory 205 may include any suitable non-transitory computer readable storage medium storing computer-readable instructions 207 executable by processing device 201 for performing the operations described herein. Although one memory device 205 is illustrated in FIG. 2, in some examples, computer system 200 may include two or more memory devices (e.g., dynamic memory and static memory).

Computer system 200 may include communication interface device 213, for direct communication with other computers (including wired and/or wireless communication), and/or for communication with network. In some examples, computer system 200 may include display device 215 (e.g., a liquid crystal display (LCD), a touch sensitive display, etc.). In some examples, computer system 200 may include user interface 217 (e.g., an alphanumeric input device, a cursor control device, etc.).

In some examples, computer system 200 may include data storage device 209 storing instructions (e.g., software) for performing any one or more of the functions described herein. Data storage device 209 may include any suitable non-transitory computer-readable storage medium, including, without being limited to, solid-state memories, optical media and magnetic media.

Figure 3:
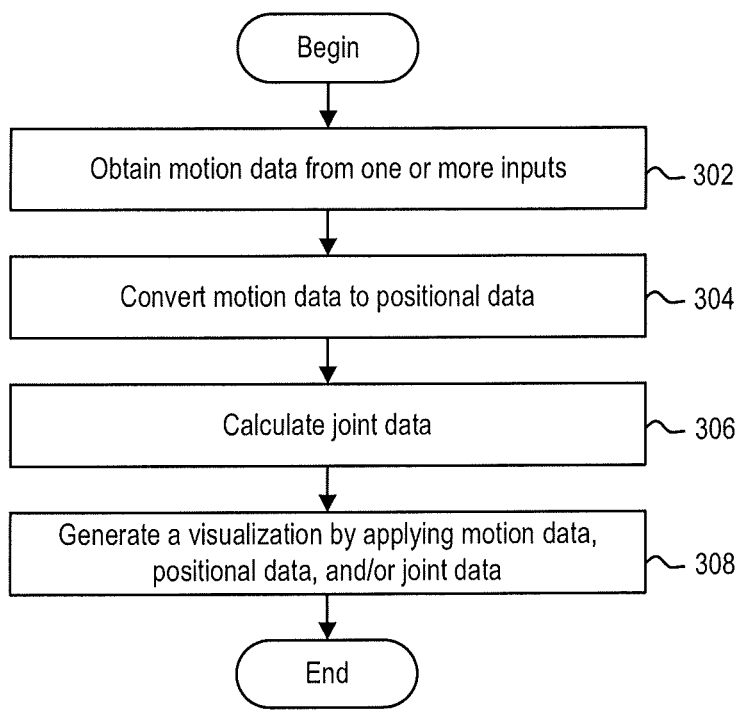
FIG. 3 is a flow diagram showing a process for generating a graphical representation of a user's body based on motion data obtained from a plurality of sensors attached to the user, according to an embodiment of the present disclosure.

FIG. 3 is a flow diagram illustrating a method 300 for generating a visualization for a character profile (3D avatar, wireframe or overlay) that may be representative of a user's body motion, according to one exemplary embodiment. Method 300 may begin at step 302.

At step 302, server system 102 may receive motion data from one or more input devices. For example, server system 102 may receive motion data from one or more sensors 106 positioned on or proximate to a body of user 112. Server system 102 may further receive motion data from one or more camera devices 107 capturing movement of user 112. Server system 102 may receive the motion data via network 110. In some embodiments, visualization module 102c may receive the motion data captured by one or more sensors 106 via sensor module 102a. In some embodiments, visualization module 102c may receive motion captured by one or more camera devices 107 via camera module 102b.

In some embodiments, sensor module 102a and camera module 102b may transmit motion data to visualization module 102c in real-time or near real-time. In some embodiments, sensor module 102a and camera module 102b may transmit motion data to visualization module 102c periodically (i.e., at pre-defined points during the day). In some embodiments, sensor module 102a and camera module 102b may transmit motion data only when prompted by visualization module 102c.

At step 304, server system 102 may convert the received motion data to positional data. For example, visualization module 102c may converted to the received motion data to positional data that describes to the position of one or more joints, limbs, and/or other reference points on the user's body.

In some embodiments, converting sensor motion data to positional data may be based on sensor 106 location, dimensions of the user's body, and/or dimensions of clothing worn by the user. Positional data may be used to locate one or more joints of interest such as elbow, wrist, shoulder, hip, knee, and ankle.

In some embodiments, visualization module 102c may convert motion data to positional data via one or more coordinate transformations. For example, sensor motion data, represented as (roll, pitch yaw) values, may be converted to 3D Cartesian positional data (e.g., (x, y, z) values) using forward kinematics. In some embodiments, motion data received from the input devices may be converted from (roll, pitch, yaw) values into a Quaternion representation. In some embodiments, motion data represented as Quaternions may then be converted to positional data and/or joint data.

At step 306, server system 102 may calculate joint data may be calculated based on at least one of the motion data and positional data. Visualization module 102c may obtain joint data from positional data by analyzing the orientation of one or more sensors with respect to the user's limbs and joints. In some embodiments, this may require knowledge of a user's limb length. This may include limb calculations based on a user's height and weight. In some embodiments, visualization module 102c may calculate joint data based, in part, on statistical population information and anatomy research.

Joint data may include a measure of the angle formed at a joint by two limbs that connect at the joint. In some embodiments, calculating the angle formed at the joint may be based on a triangulation of the angle formed by the position of at least two sensors 106 with respect to the floor or another reference point.

In some embodiments, calculating the angle formed at the joint may be based on a triangulation of the angle formed by the position of the at least two limbs with respect to the floor or another reference point.

In some embodiments, visualization module 102c may calculate an angle for the joint of interest based on the angle formed by two three-dimensional vectors at the joint of interest. The angle for the joint may be calculated using mathematical techniques, such as, dot products operations, inverse trigonometric functions, radians-to-degrees conversion, and the like.

In some embodiments, joint data may further include a "between" value representative of the angle between a target joint and the next adjacent joint to the target joint. Visualization module 102c may calculated the between value based on the angle between two directional vectors. The first directional vector may be calculated by subtracting the position of the previous adjacent joint from the position of the target joint. The second directional vector may be calculated from subtracting the position of the target joint from the position of the target joint.

In some embodiments, joint data may further include an "extend" value representative of the angle between the direction of the target joint to the next adjacent joint to the target joint. Visualization module 102c may calculate the extend value based on an angle between two directional vectors. The first directional vector may be calculated by subtracting the position of the target joint from the position of the previous adjacent joint. The second directional vector may be calculated from subtracting the position of the target joint from the position of the target joint.

In some embodiments, joint data may further include an "axis" value representative of the measure of the angle formed by the target joint when compared to a given axis. In some embodiments the axis value may include a feature that allows a three-dimensional vector to offset the calculation and provide a customized measure of the angle. Visualization module 102c may calculate the axis value using two dimensional planes to create a directional vector to measure against the angle in three-dimensional space.

At step 408, server system 102 may generate a character profile by applying one or more of the motion data, positional data, and joint data to a character profile. In one embodiment, the character profile may be stored in the database 104.

Figure 4:
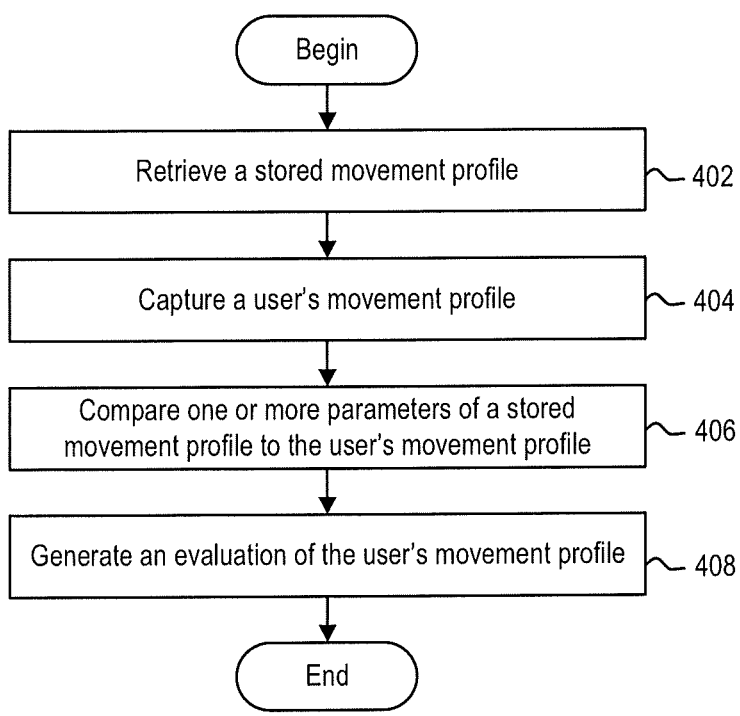
FIG. 4 is a flow chart showing a process for evaluating a user's body motion based on motion data obtained from a plurality of sensors attached to the user, according to an embodiment of the present disclosure.

FIG. 4 is a flow diagram illustrating a method 400 for evaluating a user's body motion based on motion data obtained from a plurality of sensors attached to the user, according to an exemplary embodiment.

The one or more steps discussed in conjunction with method 400 may provide an objective evaluation of a user's movement by comparing a new recorded user movement with an "ideal" movement. In some embodiments, the "ideal" movement may be a recording of a movement performed by a professional athlete or physical therapist stored in the exercise repository 104*a*. In some embodiments, the new recorded user movement may be compared with a user's past recorded movements stored in the user history repository 104*c*.

At step 402, the output generation module 102*d* of the server system 102 may retrieve a stored motion profile from the database 104 via the database management module 102*e*. The stored motion profile may be a part of the exercise repository 104*a* and/or the user history repository 104*c*. In one embodiment, the stored motion profile that is used for the evaluation may be specified by a user (patient/athlete), physical therapist, medical professional or the like. The stored motion profile may be specified thru an interactive graphical user interface, application and the like. In one embodiment, the user, physical therapist, or medical professional who specifies the stored motion profile to use may use a search feature that identifies the stored movements in the database 104 that may be used as a part of the evaluation.

At step 404, output generation module 102*d* may retrieve a character profile generated for the user. For example, output generation module 102*d* may retrieve the character profile generated above, in conjunction with method 300. Output generation module 102*d* may extract a motion profile from sensor motion data received from one or more wireless sensors configured to obtain motion information for a user by way of the visualization module 102*c* in accordance with the methods discussed above.

At step 406, an evaluation module 102*f* of server system 102 may then objectively evaluate the extracted motion profile by comparing the stored motion profile with the extracted motion profile in another step 405. For example, evaluation module 102*f* may compare position data, angle range of the joint, velocity, acceleration, jerk, and peak spread or the furthest angle of separation between the two limbs at the joint of the extracted motion profile to position data, angle range of the joint, velocity, acceleration, jerk, and peak spread or the furthest angle of separation between the two limbs at the joint of the stored motion profile.

At step 408, evaluation module 102*f* may then generate an evaluation of the newly recorded user movement. The objective evaluation of the extracted motion profile may involve a comparison of one or more parameters of the extracted motion profile with that of the retrieved predefined target motion profile. Possible parameters may include position data, angle range of the joint, velocity, acceleration, jerk, and peak spread or the furthest angle of separation between the two limbs at the joint.

In addition to providing an objective measure of a person's movement, the evaluation module 102*f* may provide an objective means for identifying points of pain or difficulty in a patient or athlete's movement by locating points within the movement that are not smooth in a trace of the movement over time.

Figure 5:
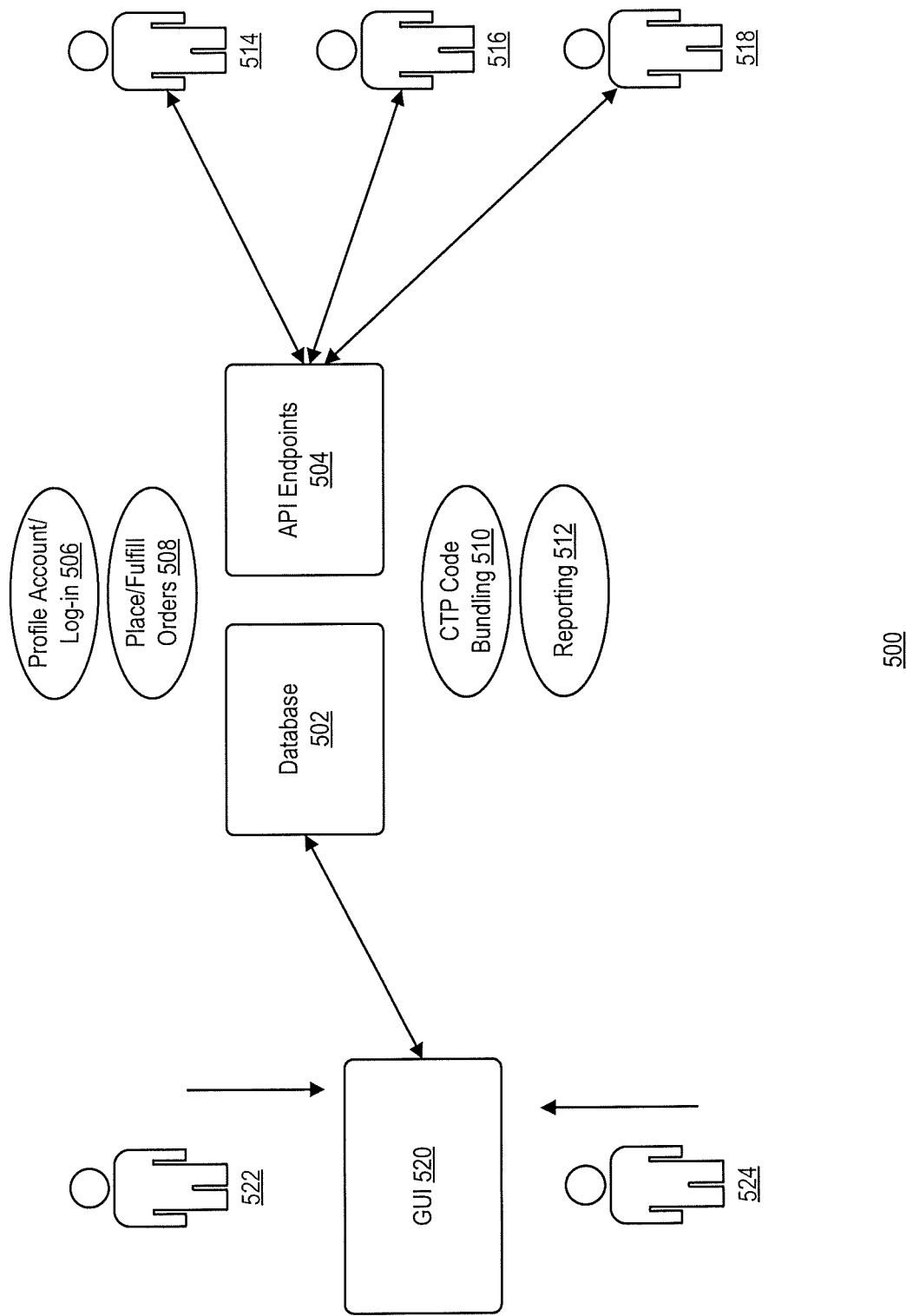
FIG. 5 is system diagram showing a body motion evaluation system, according to another embodiment of the present disclosure.

FIG. 5 is system diagram showing a body motion evaluation system 500, according to an exemplary embodiment. Body motion evaluation system 500 includes a database 502, application programming interfaces (API) endpoints 504, a user account module 506, an orders module 508, a medical code module 510, a reporting module 512, and one or more graphical user interfaces (GUIs) 520.

As illustrated a user such as an athlete or patient 522 may access the body motion evaluation system 500 by way of a graphical user interface 520. A different graphical user interface may be provided to a clinician 524 having administrative privileges. Based on their login information 506, the athlete or patient 522 and clinician 524 may be privy to different portions of the database 502, also known as a "web locker." The body motion evaluation system 500 may include the ability for users to place or fulfill orders 508 such as providing a user with a prescription for a physical therapy regimen. The system 500 may also report user compliance (participation in a prescribed physical therapy regimen) to an insurance company by way of the reporting module 512. The system 500 may also be configured to bill an insurance company for the movements included in the prescribed physical therapy regimen by way of a medical code module 510. The system may also include one or more application programming interfaces 504 that allow the system 500 to communicate with administrative computers 514, patient sensors 516 and insurance companies 518.

Figure 6:
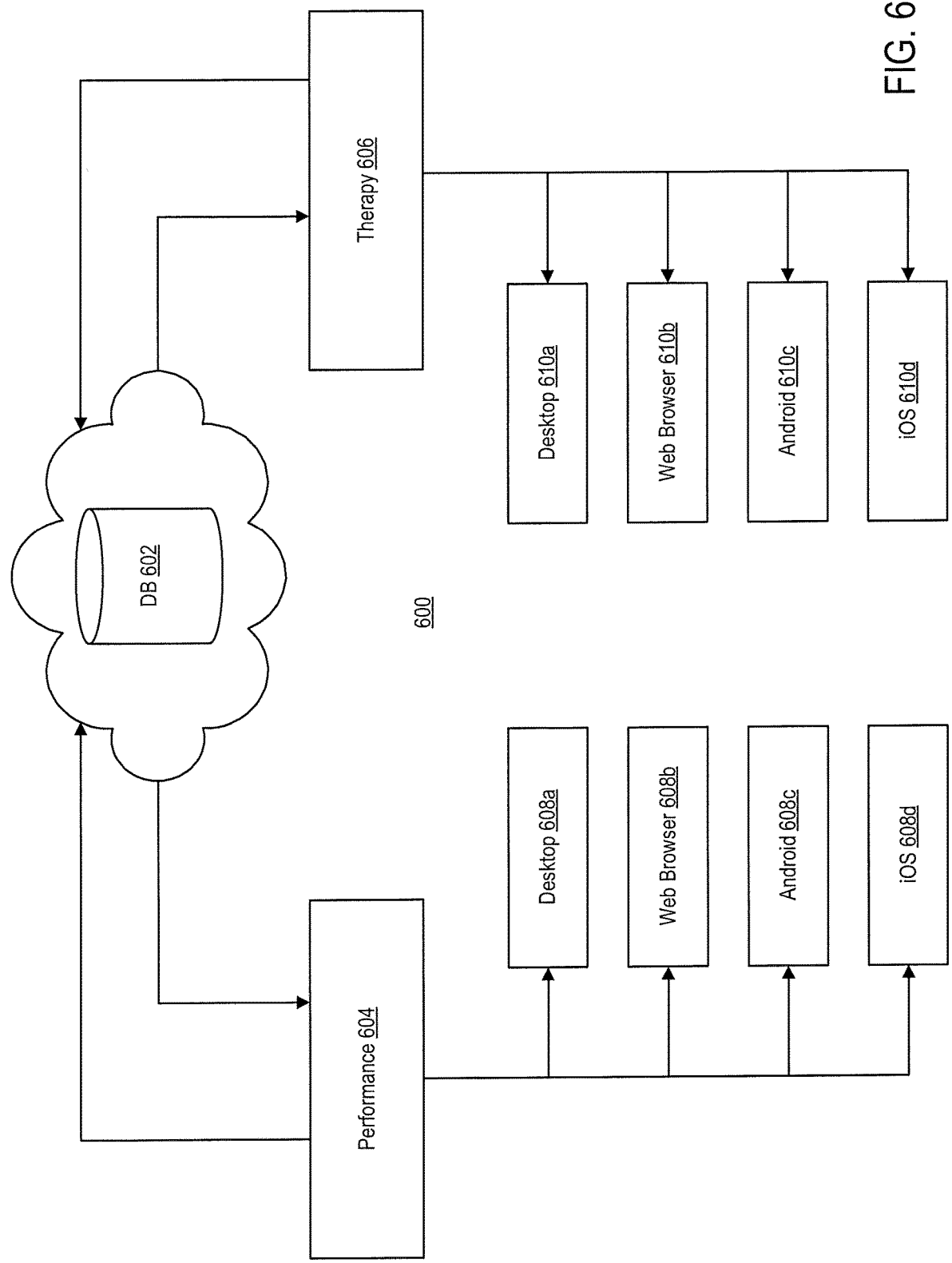
FIG. 6 is system diagram showing a body motion evaluation system, according to another embodiment of the present disclosure.

FIG. 6 is system diagram showing a body motion evaluation system 600, according to another embodiment of the present disclosure. The body motion evaluation system 600 includes a database 602, a performance module 604, and a therapy module 606. In one embodiment the performance module 604 may be configured to improve the performance of an athlete. In one embodiment the therapy module 606 may be configured to provide physical therapy to an athlete or patient. The performance module 604 may be configured to interface with users by way of a desktop 608*a*, web browser 608*b*, Android® application 608*c*, or Apple® based operating systems 608*d*. The therapy module 606 may be configured to interface with users by way of a desktop 610*a*, web browser 610*b*, Android® application 610*c*, or Apple® based operating systems 610*d*.

FIGS. 7-21 show illustrative user interfaces (UIs) that may be used within a body motion evaluation system, according to embodiments of the present disclosure.

Figure 7:
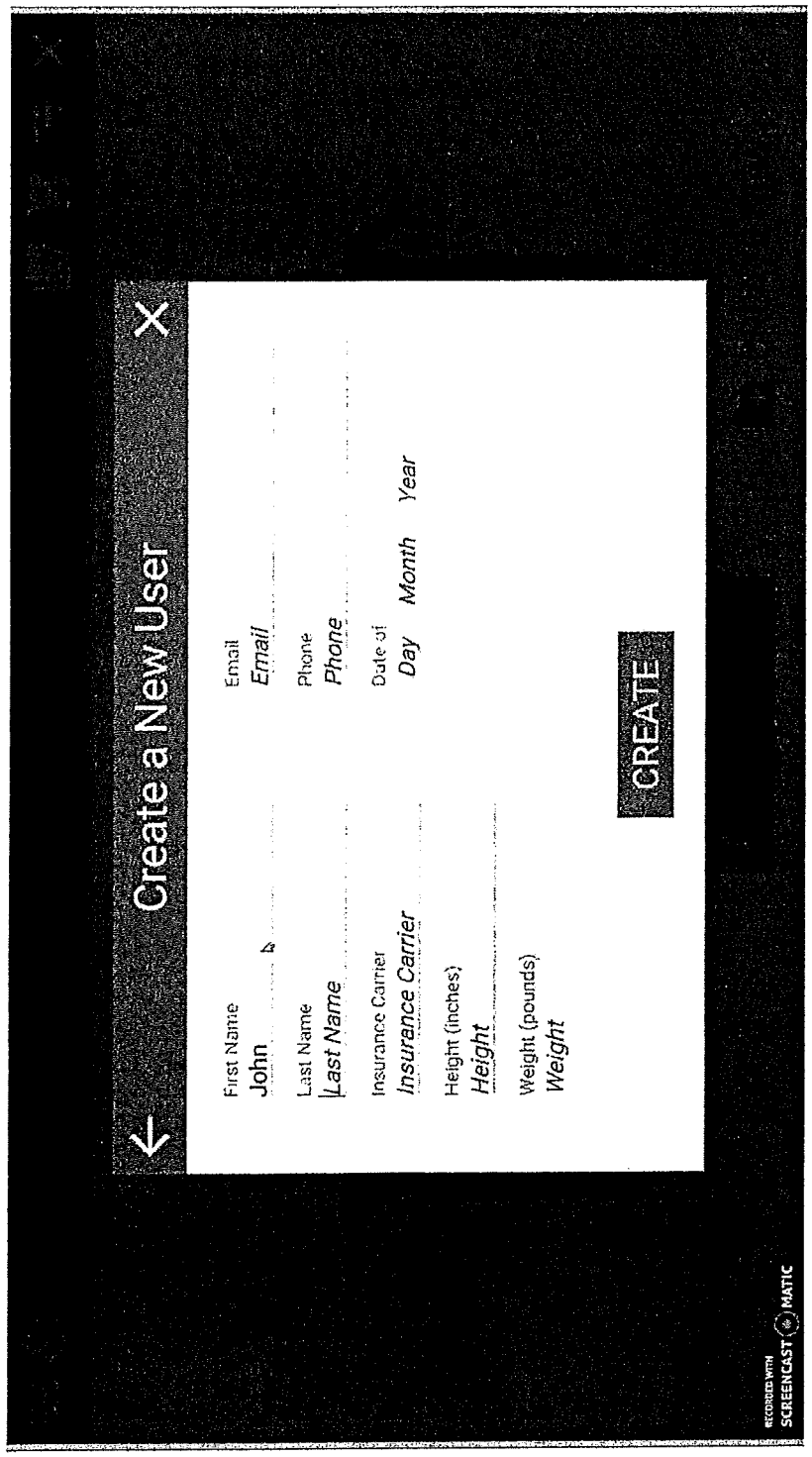

As depicted in FIG. 7 in one embodiment, a user may be asked to create a profile that includes information including their insurance carrier, height, and weight. The insurance carrier information may be used in order to automatically bill insurance companies for physical therapy treatments. The height and weight information may be used to generate the joint data from the positional data and/or sensor motion data. In one embodiment the user information provided when creating a profile may be stored within a user history repository 104*c* and configure settings in the billing information repository 104*b*.

Figure 8:
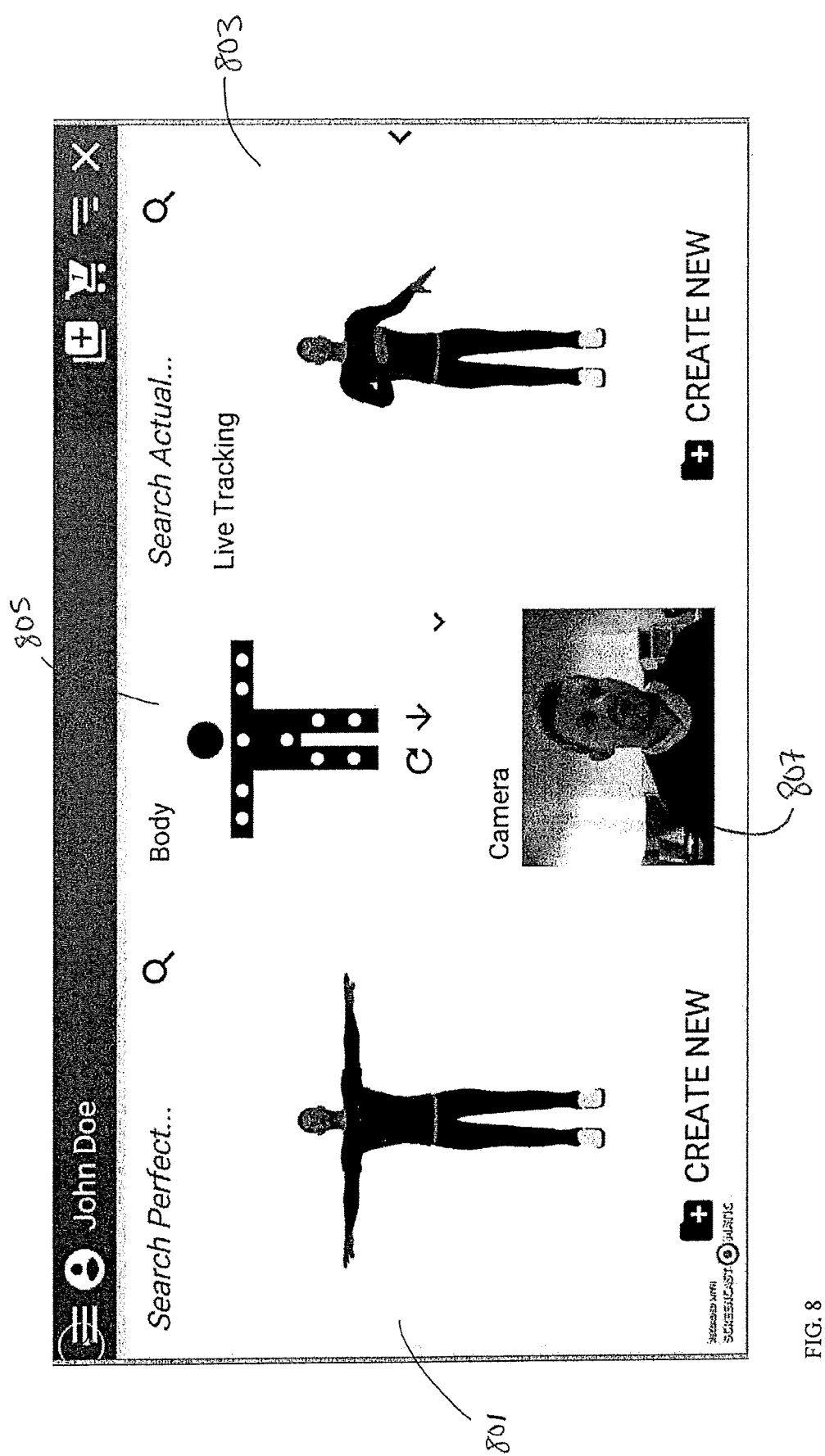

As depicted in FIG. 8 the user may be routed to an user interface that contains one or more panels providing information related to the system and methods for evaluating body motion. In one embodiment, a first panel 801 may provide a representation of an "ideal" motion, a second panel 803 may provide a live tracking representation of a user's current body position, a third panel 805 may provide a representation of the sensors located on the user's body and a fourth panel 807 may provide information related to the cameras.

Figure 9:
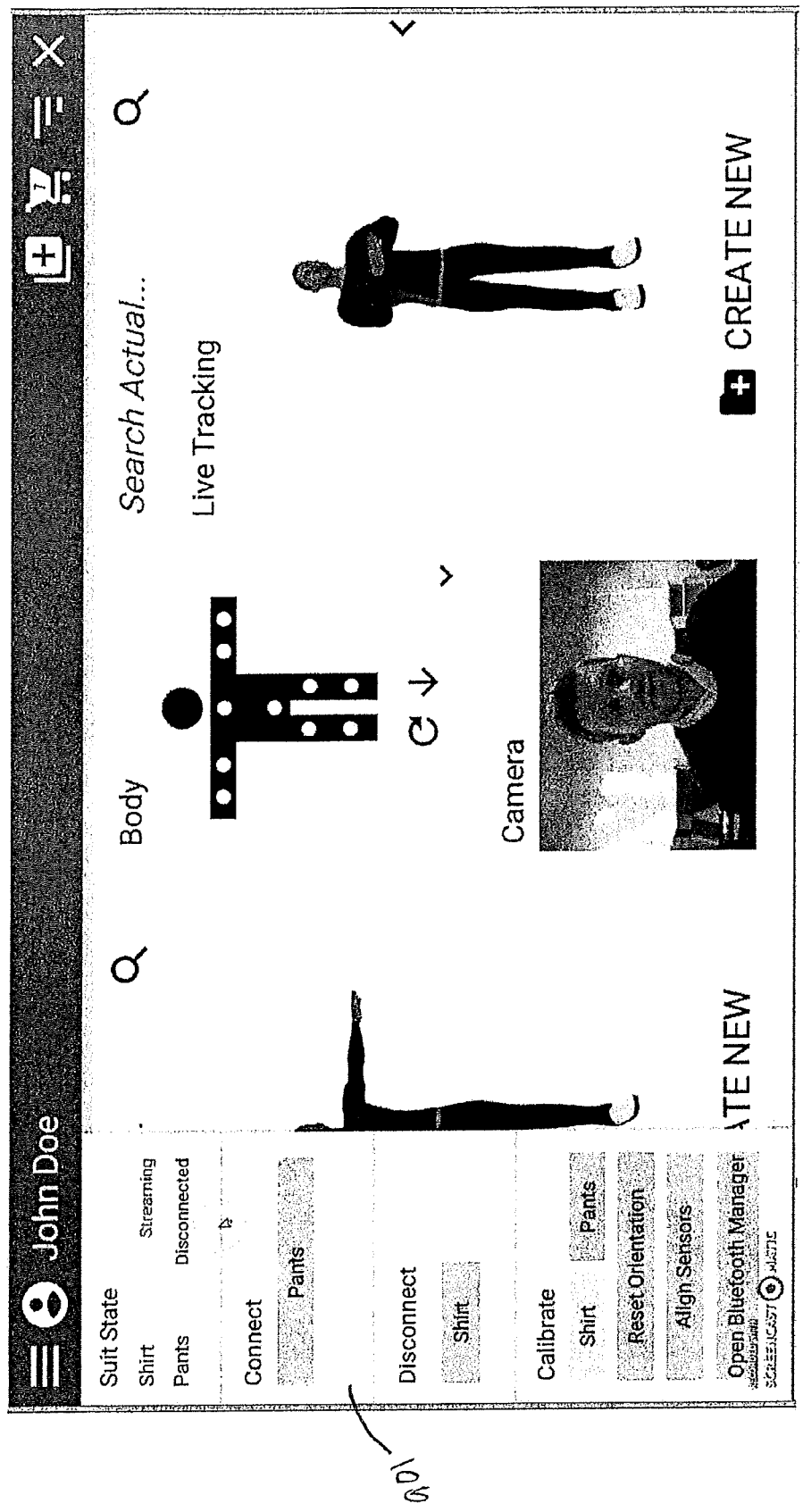

As illustrated in FIG. 9 in one embodiment the user interface may be configured with a menu bar 901 that displays information related to the state of the sensors. For example, as depicted the sensors on the shirt are streaming information while the sensors in the pans are disconnected. The menu bar 901 may include options to calibrate the wireless sensors, reset the orientation, align the sensors, and manage Bluetooth® data transfer settings.

Figure 10:
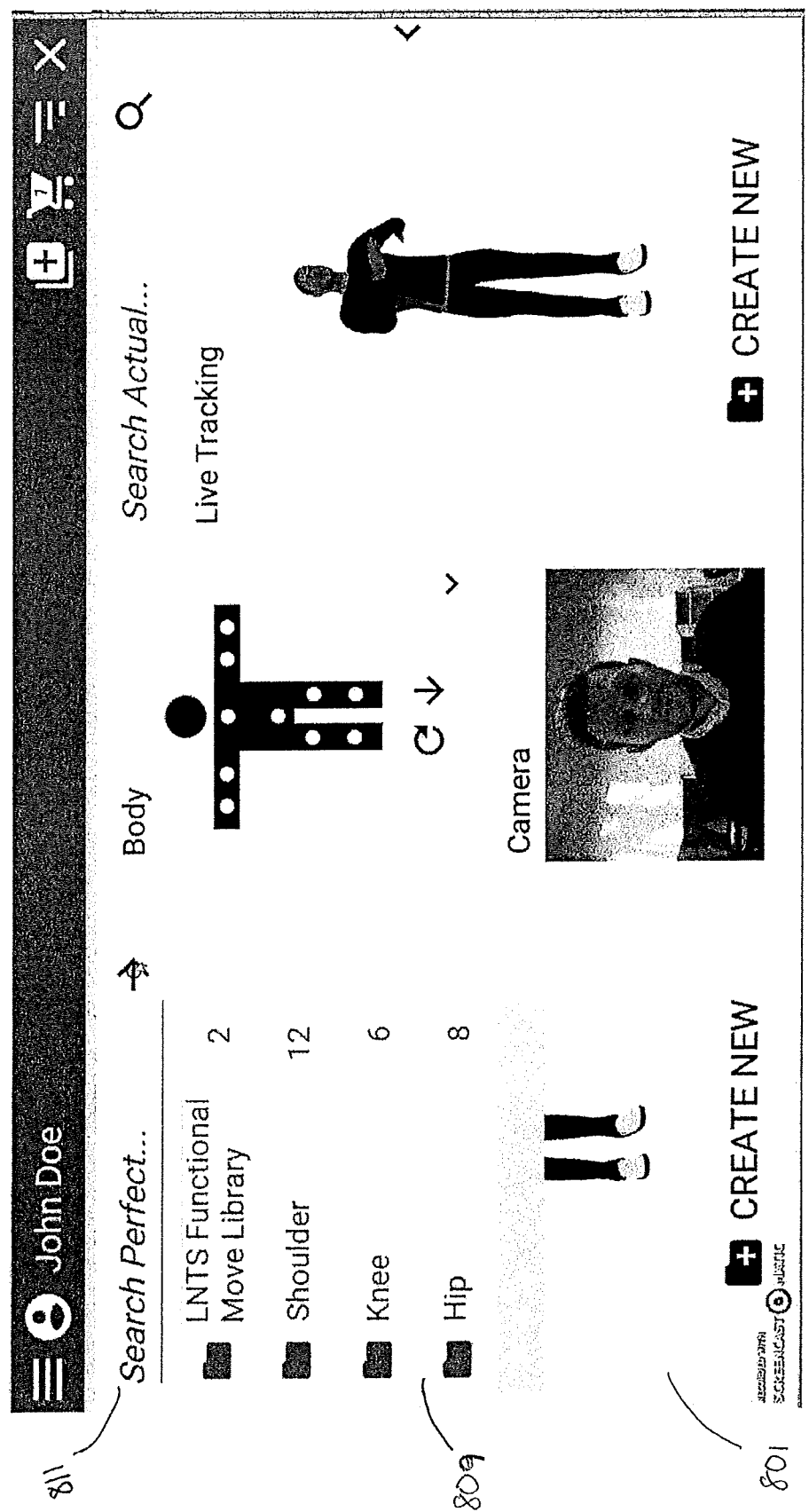

As discussed above in one embodiment the first panel 801 may provide a representation of an "ideal" motion. A representation may include a video recording, a wireframe animation, a 3D avatar animation, an overlay animation, and the like. As illustrated in FIG. 10 the "ideal" motion may be selected from one or more stored motions. For example, the user interface may provide a drop down menu 809 that allows a user to select stored motions corresponding to a particular joint such as the shoulder, knee, or hip or belonging to a particular set of motions such as a functional movement library. In one embodiment, the user may be able to search 811 thru a collection of stored motions to locate an "ideal" motion. In one embodiment the stored motions may be located in an exercise repository 104A of the database 104. In one embodiment, the "ideal" motion may correspond to a previously captured user motion that is stored in a user history repository 104c of the database 104.

As illustrated in FIG. 11 the user interface may be configured to display a recording of the representation of the selected "ideal" motion in a first panel 801. The user may also select a joint or sensor of interest 805a in the second panel 805. In response to the user's selection, the angle formed by the selected joint or sensor of interest may be calculated and displayed 801a for the "ideal" motion in a first panel 801, and the angle for the selected joint or sensor of interest may also be calculated and displayed 803a for the user's motion in real-time 803. In the depicted example, a user has opted to view the angle information for the shoulder. In one embodiment, the user may also adjust the orientation of the representation (i.e., the 3D avatar, wireframe, or overlay) so that the joint or sensor of interest is more clearly visible.

Figure 12:
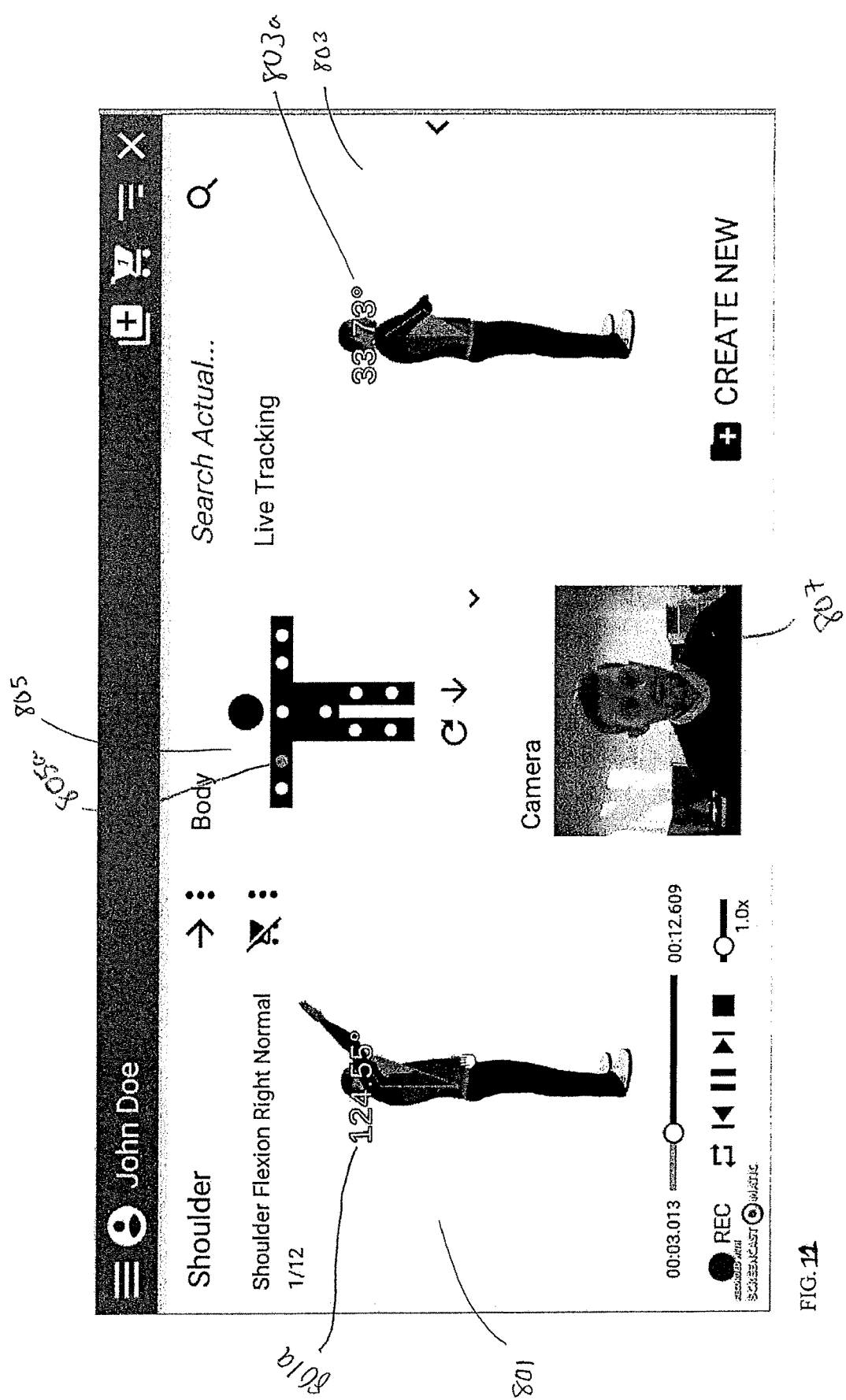
Figure 12:
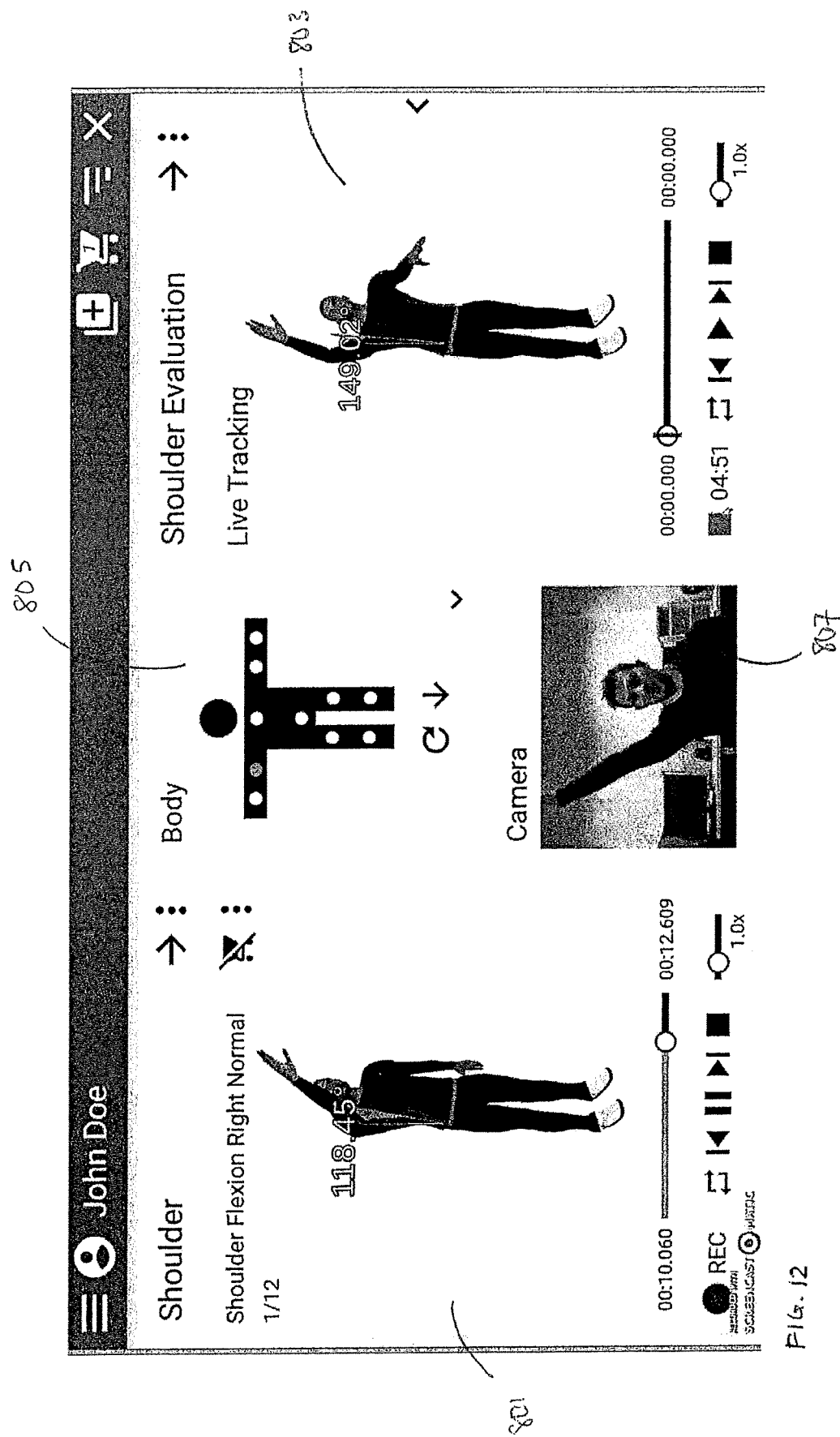

As illustrated in FIG. 12 the user interface may be configured so that a user's live motion is recorded and available for playback in the second panel 803. Accordingly, a user may be able to play a recording of the "ideal" motion synchronized with a recording of the user's motion.

Figure 13:
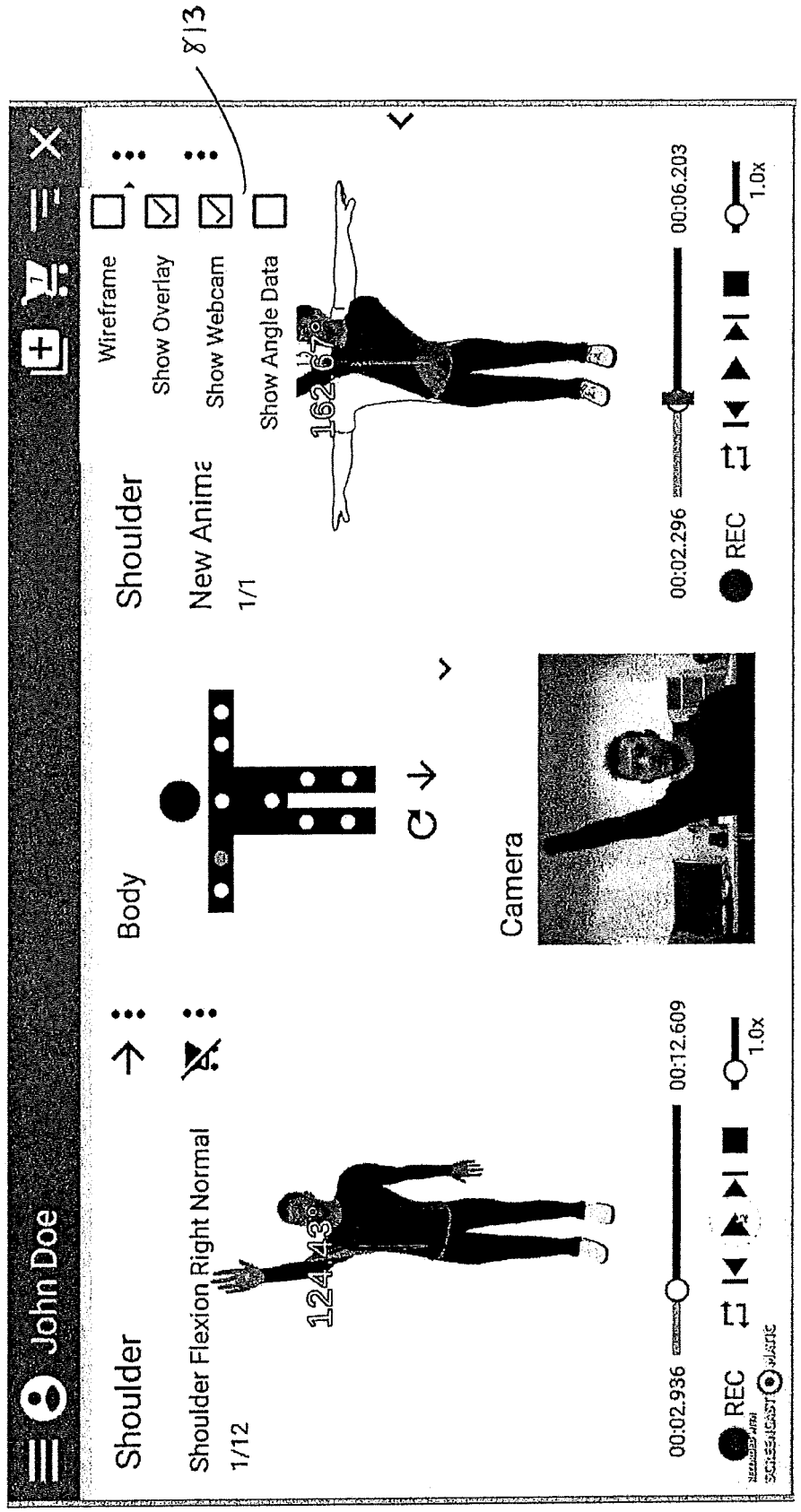

As illustrated in FIG. 13 the user interface may include a motion representation settings panel 813 that allows a user to select the character representation they would like to see for the "ideal" motion and/or the user motion. As depicted the character representation may be a wireframe, overlay, or 3D avatar. The motion representation settings panel 813 may also include the option of displaying camera data from a webcam that populates panel 807 and angle data that may be superimposed on the motion representations of the "ideal" motion and the user motion.

Figure 14:
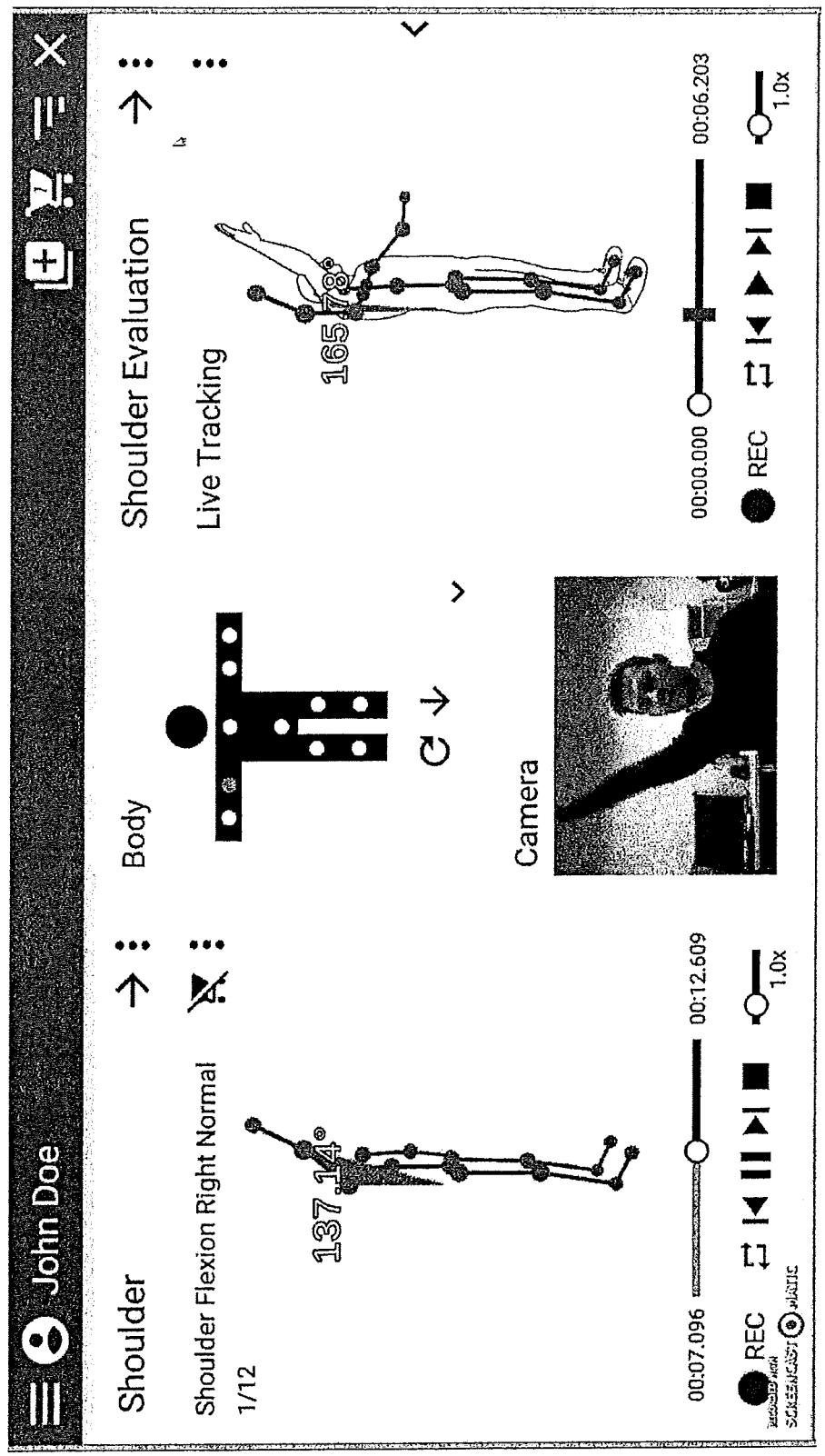

As illustrated in FIG. 14 "ideal" motion and/or user motion may be represented as a wireframe and/or overlay. As illustrated with regards to the "ideal" motion, the shoulder flexion angle may be calculated based on a triangle drawn between the arm, a position on the user's body, and the joint of interest, the shoulder.

Figure 15:
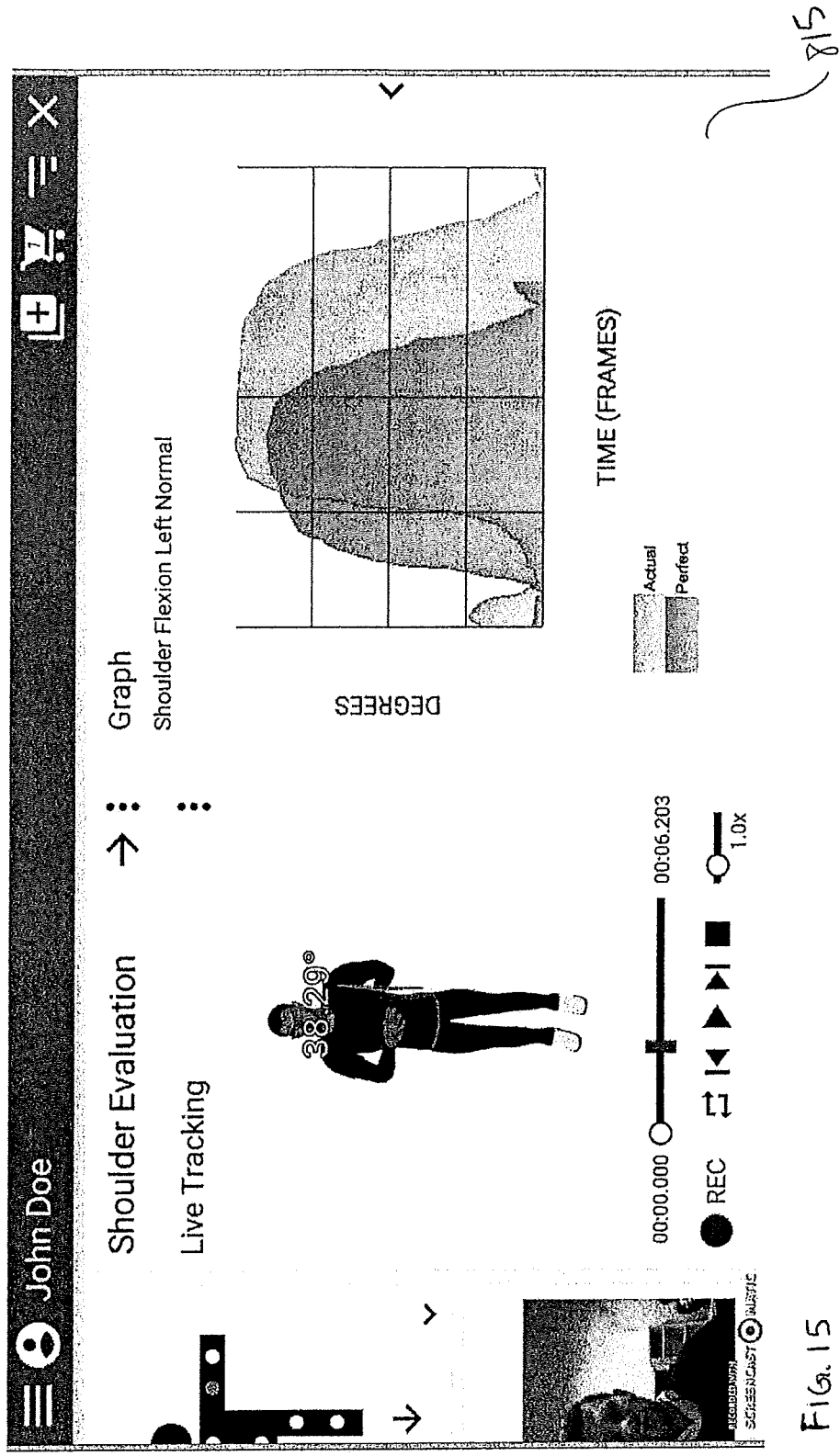

As illustrated in FIG. 15 the user interface may include an evaluation panel 815 that provides a graphical representation comparing a user's recorded movement with an "ideal" movement. As illustrated, the comparison may display the angle of interest over time in degrees per frame. Suitable comparison parameters may also include position, velocity, acceleration over time.

Figure 16:
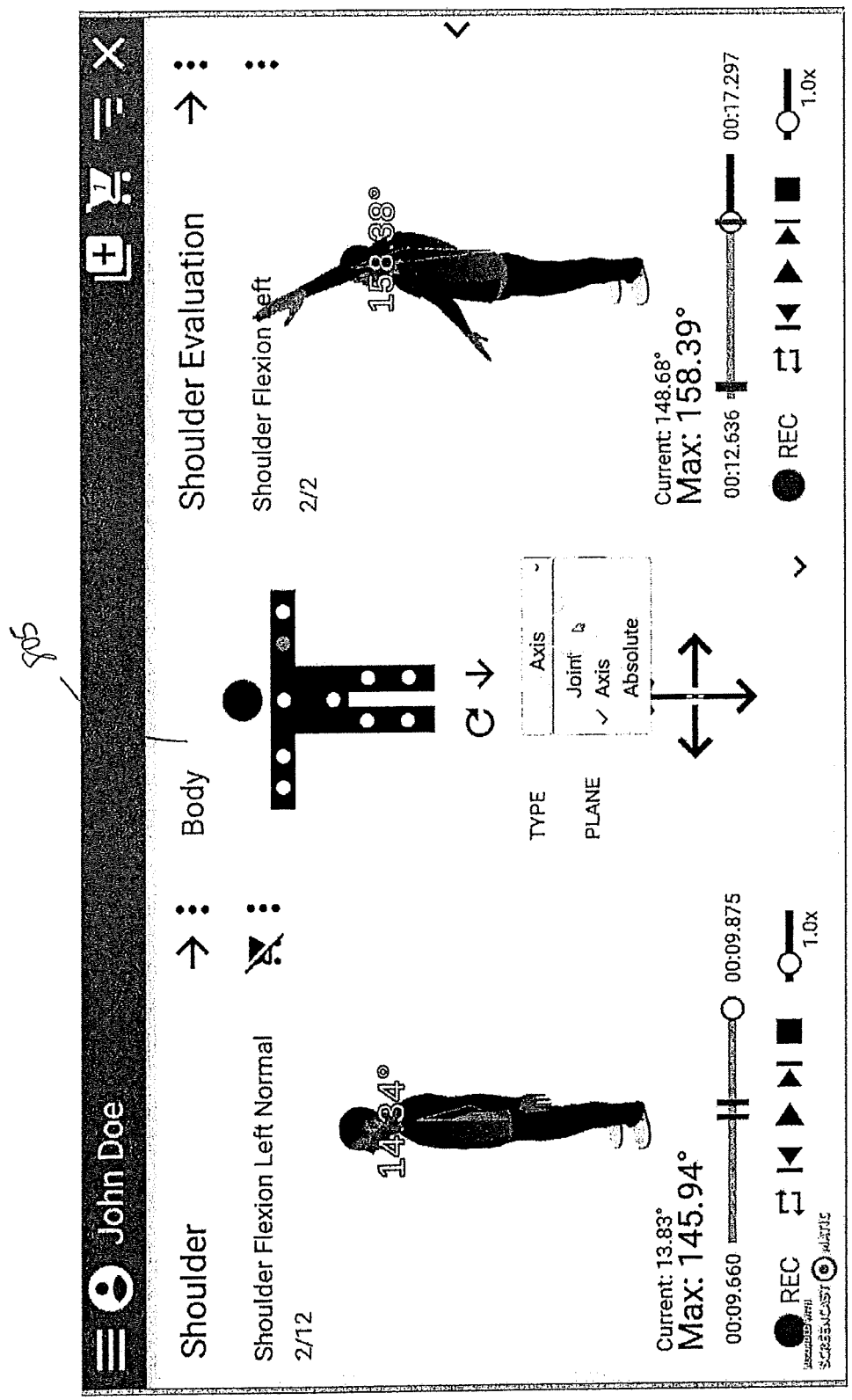

As illustrated in FIG. 16 the third panel 805 providing a representation of the sensors located on the user's body may also include one or more menus that allow a user to select various configurations for measuring the angles of interest.

Figure 17:
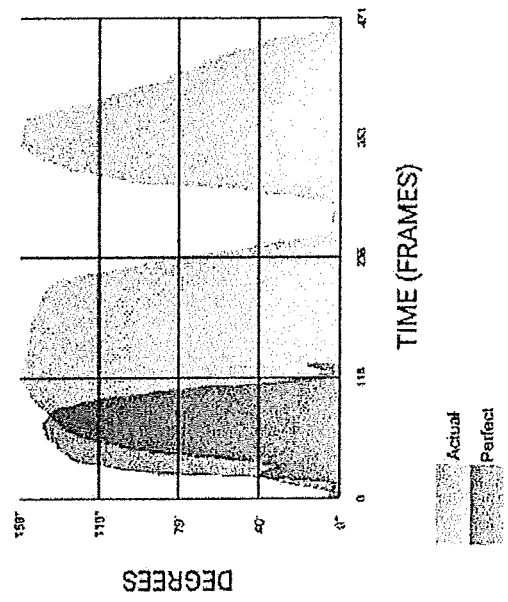

As illustrated in FIG. 17 in one embodiment the user interface in connection with the output generation module 102d may produce an evaluation or report. The evaluation may provide a comparison of the user's recorded movement with an "ideal" movement. In one embodiment the evaluation may display the user's personal information, the time and date of the report was generated, the time and date of the movement being evaluated, the movement of interest, the timing for the movement of interest, where the measurement was taken from, what the maximum angle of measurement was and a graph comparing the user's recorded movement with an "ideal" movement. The graph may display the angle of interest over time in degrees per frame, position, velocity, and/or acceleration over time. From the graph it may be possible to identify points of pain based on the shape of the graph. The evaluation or report may also include timestamping so the user may see the routine of the duration and frequency of exercise. This may allow a user's progress to be tracked per session and over selected extended periods of time (e.g. day, week, month, year).

Figure 18:
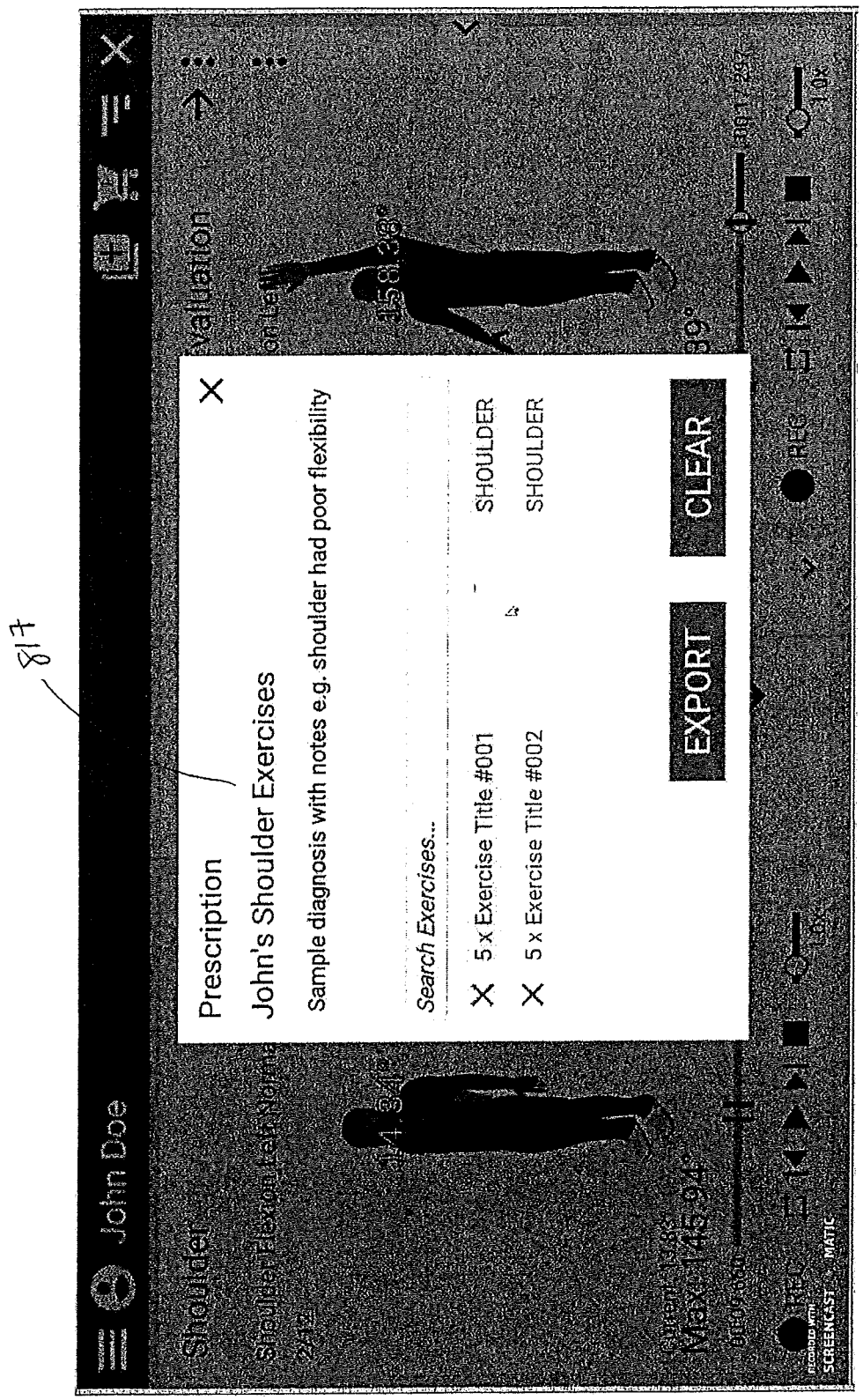

As illustrated in FIG. 18 in one embodiment a clinician such as a physical therapist or trainer may use the user interface to prescribe a series of exercises for a patient or athlete to complete. The clinician may input information regarding the user's condition, and select one or more exercises that are stored in the exercise repository 104A in the depicted prescription portal 817. The data input by the clinician may then be exported into prescription email, or prescription document that is provided to the user.

For example, as illustrated in FIG. 19, the prescription document 1900 may be automatically generated based on the selections made by the clinician. The prescription document 1900 may automatically include a description and images that correspond to the selected exercises.

Figure 20:
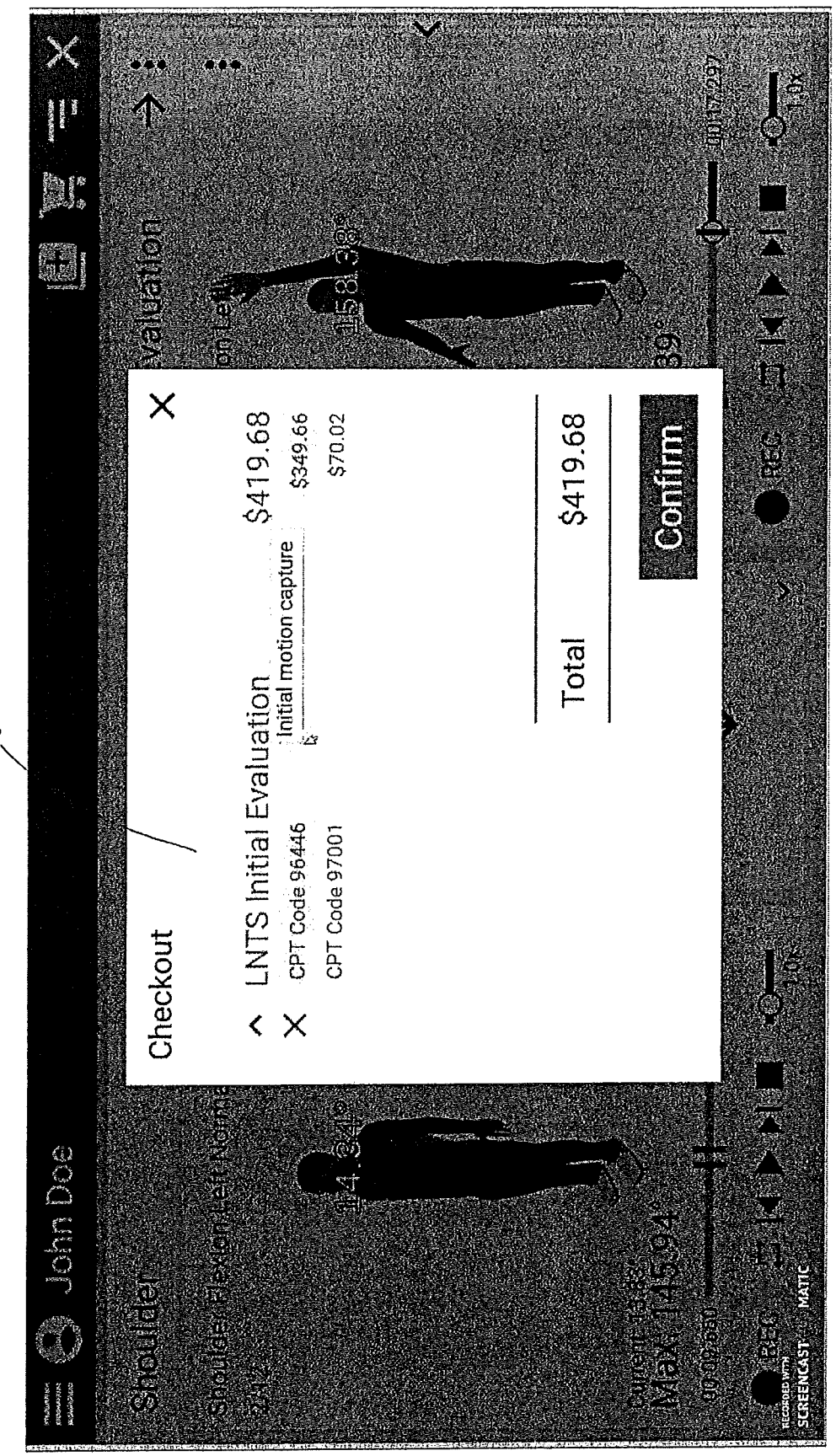

As illustrated in FIG. 20 the user interface may also include a billing portal 2000. Using the billing portal, a clinician or user may select one or more exercises that were performed with the user. The billing portal 2000 may retrieve billing information such as CPT codes from the billing information repository 104b in order to automatically generate an invoice compatible with insurance company computing systems.

Figure 21:
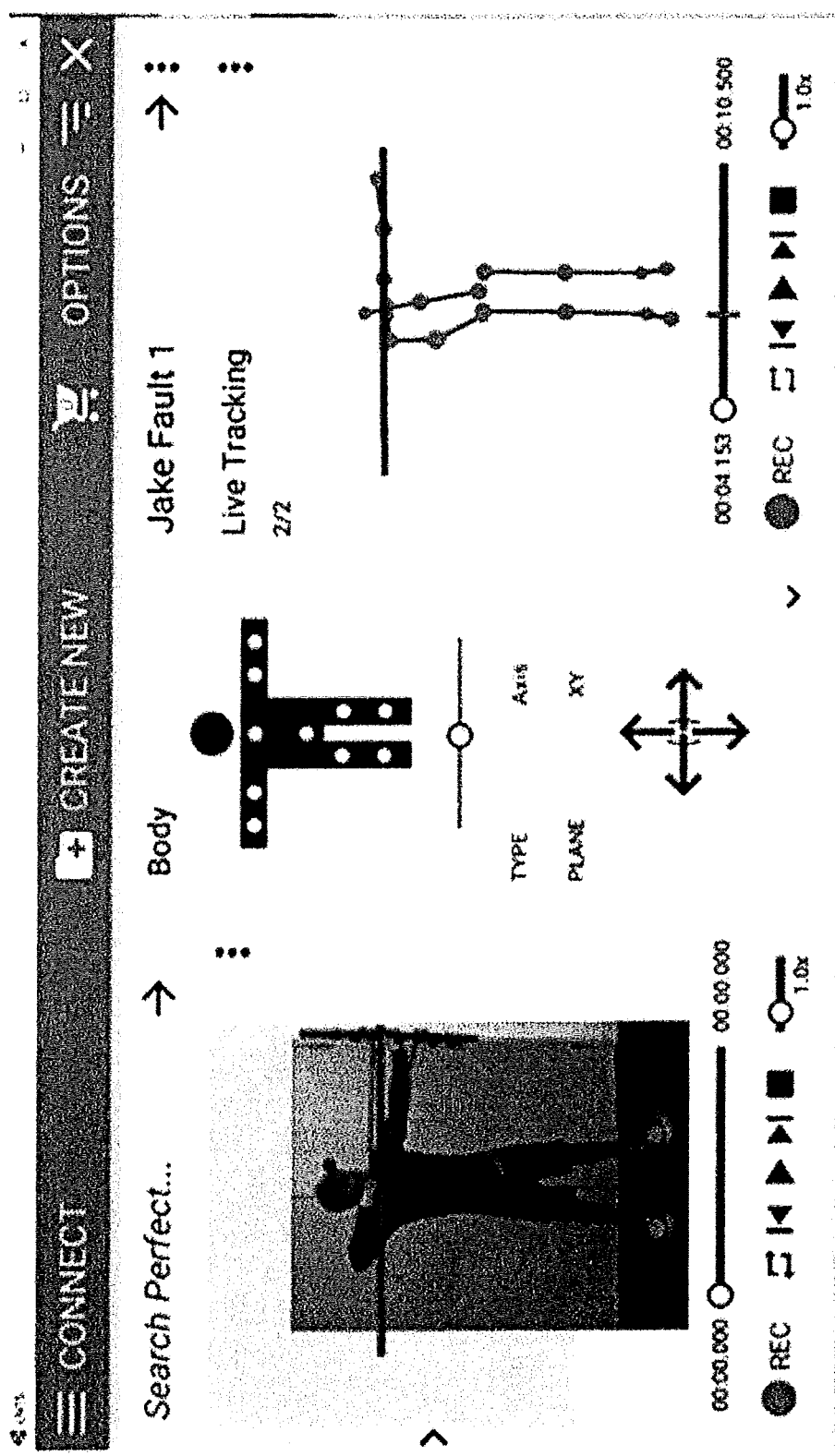

As illustrated in FIG. 21 the user interface may also be used for sports-specific performance training applications corresponding to the performance module 604. The user interface that displays a target sports specific ideal motion and a live tracking of athlete motion. In one embodiment the user interface may be configured differently for a sports-specific performance training application corresponding to the performance module 604 than for a therapy based application.

In one embodiment the output generation module may generate applications specific to a user. User specific applications may be tailored to the needs of the veterans rehabilitation market, the fitness and athletic improvement market, the mobile and personal device digital products market and the medical market.

In one embodiment the systems and methods described herein may be used as a baseline diagnostic and informational tool within a hospital or other medical care environment. For example, the systems and methods described herein may be used in connection with regenerative medicine groups as a means to track the effect of and outcomes from stem cell injections or other physical therapy treatments. Additionally, the user compliance and billing aspects of the systems and methods described herein may be useful for medical care provided in connection with worker's compensation.

In one embodiment the systems and methods described herein may be used as a supportive pre- or post-op information resource for orthopedics or other medical professionals. For example, the systems and methods described herein may be used in an in-home setting and allow for in-home rehabilitation after orthopedic surgery. With conventional in-home rehabilitation or center based rehabilitation often times physical therapy is unsuccessful in aiding a patient or athlete in obtaining their full range of motion due to non-compliance and lack of oversight from medical professionals. As a result, many patients and athletes may undergo second corrective surgeries. The systems and methods described herein may provide remote tracking, and guided physical therapy routines with oversight from medical professionals, thus assisting with patient and athlete compliance and providing an improved quality of physical therapy.

In one embodiment the systems and methods described herein may be used by wellness providers such as physical therapists, masseuses or chiropractors. In one embodiment the wellness providers may track patient/client motion prior to, during, and after treatment and provide the information to patients and clients using the systems and methods described herein.

In one embodiment the systems and methods described herein may be provided to primary care physicians as a part of routine patient monitoring during yearly examinations.

In one embodiment, the systems and methods described herein may involve one or more of the following steps in any suitable order. In one step a user may putt on a body suit containing wireless sensors. In one step the sensors on the body suit may be paired to a computing device. In one step a user may select a target or ideal motion profile for comparison. In one step the body suit may starting a recording of a user's movement while the user is wearing the suit. In one step the suit transmits data to the computing device while recording the user's movement. In one step angle data is recorded based on the target joint and measurement type. In one step a suit may stream data to the computing device. In one step rotational data corresponding to the shirts or pans of the body suit may be transmitted over Bluetooth® or other suitable communication protocols to an application. In one step rotational data (in Quaternions) may be applied to corresponding joints of a character profile (e.g., 3D avatar).

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

The invention claimed is:
1. A computer-implemented method comprising:
receiving, by a server system, motion data directly from one or more sensors located on a body of a user, the motion data corresponding to movement of the user, wherein the one or more sensors preprocesses the motion data by filtering the motion data and down sampling the motion data prior to sending the motion data to the server system;
converting, by the server system, the received motion data to positional data for each joint of the user based on an orientation of each sensor with respect to each joint and limb of the user, the converting comprising:
transforming roll, pitch, and yaw coordinates of the received motion data to three dimensional positional data that illustrates one or more positions of at least one of one or more joints, limbs, and other reference points on the user's body;
generating, by the server system, a motion profile based on at least the positional data and the motion data received from the one or more sensors;
retrieving, by the server system, a pre-defined target motion profile from a database structure; and
objectively evaluating the motion profile, by the server system, by comparing one or more parameters of the generated motion profile with one or more parameters of the retrieved pre-defined target motion profile.

2. The method of claim 1, further comprising:
displaying, by the server system, a comparison between the motion profile and the retrieved pre-defined target motion profile in real-time.

3. The method of claim 1, wherein the positional data is generated while the user performs the movement.

4. The method of claim 1, further comprising:
generating, by the server system, joint data for each joint of the user based on the motion data and the positional data.

5. The method of claim 4, wherein generating the joint data based on the motion data and positional data, comprises:
analyzing the orientation of each of the one or more sensors with respect to the user's limbs and joints.

6. The method of claim 1, further comprising:
receiving additional motion data from at least one or more camera devices.

7. A computer-implemented method comprising:
receiving, by a server system, motion data directly from a one or more sensors positioned on a body of a user while performing a movement, wherein the one or more sensors preprocesses the motion data by filtering the motion data and down sampling the motion data prior to sending the motion data to the server system;
converting, by the server system, the received motion data to positional data for each joint of the user based on an orientation of each sensor with respect to each joint and limb of the user, the converting comprising:
transforming roll, pitch, and yaw coordinates of the received motion data to three dimensional positional data that illustrates one or more positions of at least one of one or more joints, limbs, and other reference points on the user's body;
generating, by the server system, a motion profile for the user based at least on the positional data and the motion data, by:
calculating a position of a joint of the user's body based on the positional data and the motion data;
calculating positions of at least two reference points of the user's body based on the positional data and the motion data; and
calculating an actual range of motion for the joint based on the position of the joint and the positions of the at least two reference points;

retrieving, by the server system, a reference range of motion from a database storing one or more reference range of motions for one or more movements; and evaluating, by the server system, a user's body motion by comparing the reference range of motion to the actual range of motion to objectively evaluate the user's movement.

8. The method of claim 7, wherein calculating the actual range of motion for the joint comprises:

forming a triangle having vertices based on the position of the joint and the positions of the at least two reference points; and calculating the actual range of motion for the joint based on a peak spread of the triangle.

9. The method of claim 7, wherein generating, by the server system, the motion profile for the user based at least on the motion data, further comprises:

calculating a position of the joint over time based on the positional data and the motion data;

calculating positions of the at least two reference points of the user's body based on the positional data and the motion data; and calculating a peak angle over time for the joint based on the position of the joint and the positions of the at least two reference points over time.

10. The method of claim 9, wherein evaluating the user's body motion comprises generating a graph of the peak angle over time for the joint.

11. The method of claim 7, wherein the reference range of motion is a range of motion previously calculated for the user.

12. The method of claim 7, wherein the reference range of motion is not associated with the user.

13. The method of claim 7, further comprising:

receiving additional motion data from at least one or more camera devices.

14. A system, comprising:

one or more sensors configured to capture a movement of a user, each of the one or more sensors are located on a body of the user;

a processor in communication with the one or more sensors; and a memory having programming instructions stored thereon, which, when executed by the processor, performs an operation, comprising:

receiving motion data directly from the one or more sensors, the motion data corresponding to movement of a user, wherein the one or more sensors preprocesses the motion data by filtering the motion data and down sampling the motion data prior to sending the motion data to the processor;

converting the received motion data to positional data for each joint of the user based on an orientation of each sensor with respect to each joint and limb of the user, the converting comprising:

transforming roll, pitch, and yaw coordinates of the received motion data to three dimensional positional data that illustrates one or more positions of at least one of one or more joints, limbs, and other reference points on the user's body;

generating a motion profile based on at least the positional data and the motion data received from the one or more sensors;

retrieving a pre-defined target motion profile from a database structure; and objectively evaluating the motion profile by comparing one or more parameters of the generated motion profile with one or more parameters of the retrieved pre-defined target motion profile.

15. The system of claim 14, further comprising:

displaying a comparison between the motion profile and the retrieved pre-defined target motion profile in real-time.

16. The system of claim 14, wherein the positional data is generated performing the movement.

* * * * *